(12) United States Patent
Morishita

(10) Patent No.: US 8,119,828 B2
(45) Date of Patent: Feb. 21, 2012

(54) MATERIAL FOR AN ORGANIC ELECTROLUMINESCENCE DEVICE AND AN ORGANIC ELECTROLUMINESCENCE DEVICE

(75) Inventor: Hironobu Morishita, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 284 days.

(21) Appl. No.: 12/519,170

(22) PCT Filed: Dec. 10, 2007

(86) PCT No.: PCT/JP2007/073749
§ 371 (c)(1),
(2), (4) Date: Jun. 15, 2009

(87) PCT Pub. No.: WO2008/072586
PCT Pub. Date: Jun. 19, 2008

(65) Prior Publication Data
US 2010/0044686 A1 Feb. 25, 2010

(30) Foreign Application Priority Data
Dec. 15, 2006 (JP) .................. 2006-338200

(51) Int. Cl.
C07C 255/47 (2006.01)
H01L 51/54 (2006.01)
(52) U.S. Cl. ........... 558/427; 564/105; 257/40; 257/98; 257/E51.027
(58) Field of Classification Search .................. 558/427; 544/343, 344; 564/105; 257/40, 98, E51.027
See application file for complete search history.

(56) References Cited

U.S. PATENT DOCUMENTS

| 4,720,432 | A | 1/1988 | VanSlyke et al. |
| 5,061,569 | A | 10/1991 | VanSlyke et al. |
| 6,566,807 | B1 | 5/2003 | Fujita et al. |
| 6,597,012 | B2 | 7/2003 | Kido et al. |
| 7,074,500 | B2 | 7/2006 | Pfeiffer et al. |
| 2005/0255334 | A1 | 11/2005 | Kang et al. |
| 2006/0024599 | A1 | 2/2006 | Jubran et al. |
| 2006/0210898 | A1 | 9/2006 | Jubran |

FOREIGN PATENT DOCUMENTS

| JP | 4-297076 | | 10/1992 |
| JP | 6-298744 | * | 10/1994 |
| JP | 8-148281 | | 6/1996 |
| JP | 11-54284 | | 2/1999 |
| JP | 11-251067 | | 9/1999 |
| JP | 3670481 | | 11/1999 |
| JP | 2000-196140 | | 7/2000 |
| JP | 2001-102173 | | 4/2001 |
| JP | 2001-297883 | | 10/2001 |
| JP | 2002-260863 | * | 9/2002 |
| JP | 2003-31365 | | 1/2003 |
| JP | 2004-514257 | | 5/2004 |
| JP | 2005-121887 | | 5/2005 |
| JP | 2007-52063 | | 3/2007 |

OTHER PUBLICATIONS

U.S. Appl. No. 12/325,052, filed Nov. 28, 2008, Morishita, et al.
U.S. Appl. No. 13/132,141, filed Jun. 1, 2011, Morishita, et al.

* cited by examiner

Primary Examiner — Shailendra Kumar
(74) Attorney, Agent, or Firm — Oblon, Spivak, McClelland, Maier & Neustadt, L.L.P.

(57) ABSTRACT

A material for an organic electroluminescence device represented by the following formula (I):

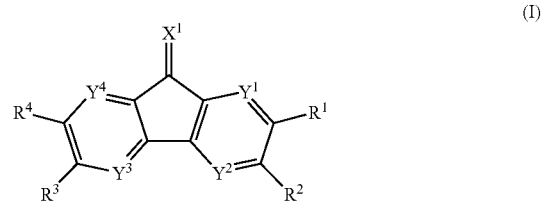

wherein $X^1$ is one of divalent groups represented by the following (a) to (e); $Y^1$ to $Y^4$ are independently a carbon atom or a nitrogen atom; and $R^1$ to $R^4$ are independently a hydrogen atom, an alkyl group, a substituted or unsubstituted aryl group, a substituted or unsubstituted heterocycle, a halogen atom, a fluoroalkyl group or a cyano group, or $R^1$ and $R^2$, and $R^3$ and $R^4$ are independently bonded to form a substituted or unsubstituted aromatic ring or a substituted or unsubstituted heterocycle.

15 Claims, 1 Drawing Sheet

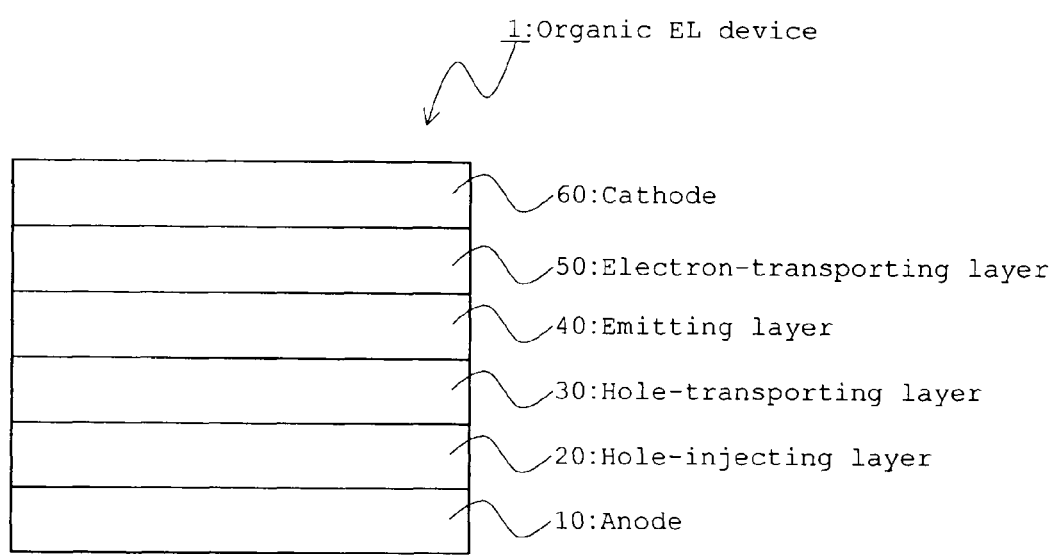

MATERIAL FOR AN ORGANIC ELECTROLUMINESCENCE DEVICE AND AN ORGANIC ELECTROLUMINESCENCE DEVICE

This application is a 371 of PCT/JP07/73749, filed Dec. 10, 2007.

TECHNICAL FIELD

The invention relates to a material for an organic electroluminescence device and an organic electroluminescence device using the same.

BACKGROUND ART

An organic electroluminescence device (hereinafter the term "electroluminescence" is often abbreviated as "EL") is a self-emission device utilizing the principle that a fluorescent compound emits light by the recombination energy of holes injected from an anode and electrons injected from a cathode when an electric field is impressed.

As the stacking structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such stack structure devices, their device structures and fabrication methods have been contrived to increase recombination efficiency of injected holes and electrons.

Conventionally, as the hole-transporting material used in an organic EL device, an aromatic diamine derivative disclosed in Patent Document 1 or an aromatic condensed ring diamine derivative disclosed in Patent Document 2 are known.

However, in an organic EL device in which such aromatic diamine derivative is used in a hole-transporting material, in order to obtain a sufficient luminance, a higher voltage is required to be applied. As a result, a problem arises that device life is shortened or power consumption is increased.

As a method for solving these problems, a method in which an electron-accepting compound such as a Lewis acid or the like is doped with a hole-injecting layer of an organic EL device is proposed (Patent Documents 3 to 9 or the like). The electron-accepting compounds used in Patent Documents 3 to 6 have, however, problems that they are unstable when handled during the production process of an organic EL device or stability such as heat resistance becomes insufficient at the time of driving an organic EL device, resulting in a shortened device life.

Tetrafluorotetracyanoquinodimethane exemplified in Patent Documents 3, 4 or the like as an electron-accepting compound has a small molecular weight and has a high degree of sublimation properties since it is substituted by fluorine. Therefore, it may be diffused within an apparatus when fabricating an organic EL device by vacuum vapor deposition, thereby to contaminate the apparatus or the device.

The inventors made intensive studies on electron-accepting compounds or the like. As a result, the inventors noticed a fluorenone derivative. A fluorenone derivative is known as an electron-transporting material of an electrophotographic photoreceptor (see Patent Documents 10 and 11).

A thioether group or the like is introduced into this derivative in order to improve compatibility with a binder resin or solubility in a solvent, which is a subject to be solved as an electrophotographic photoreceptor. Therefore, there is a possibility that decomposition or the like of the thioether portion may occur by a deposition process which is required for fabricating an organic EL device or by the Jule heat or the like which is generated at the time of driving a device. That is, this derivative is concerned for the lowering of electron acceptability or other problems when applied to an organic EL device, even though it is satisfactory as an electrophotographic photoreceptor.

Patent Document 1: U.S. Pat. No. 4,720,432
Patent Document 2: U.S. Pat. No. 5,061,569
Patent Document 3: JP-A-2003-031365
Patent Document 4: JP-A-2001-297883
Patent Document 5: JP-A-2000-196140
Patent Document 6: JP-A-H11-251067
Patent Document 7: JP-A-H04-297076
Patent Document 8: JP-T-2004-514257
Patent Document 9: US2005/0255334A1
Patent Document 10: JP-A-2005-121887
Patent Document 11: Japanese Patent No. 3670481

The invention has been made based on the above-mentioned problems, and an object thereof is to provide an electron-accepting material suitable as the material constituting an organic EL device, in particular as a hole-injecting material.

DISCLOSURE OF THE INVENTION

The inventors made studies on a material for an organic EL device, in particular, a fluorenone derivative as a material for a hole-injecting material. As a result, the inventors have found that, by allowing the quinine portion of the fluorenone derivative to be a specific structure such as a dicyanomethylene structure or a cyanoimine structure, and by improving the electron acceptability, a fluorenone derivative can be an electron-accepting material suitable for an organic EL device.

The inventors have also found that an organic EL device using these compounds can have a lower driving voltage or a longer device life.

The invention provides the following material for an organic EL device or the like.

1. A material for an organic electroluminescence device represented by the following formula (I):

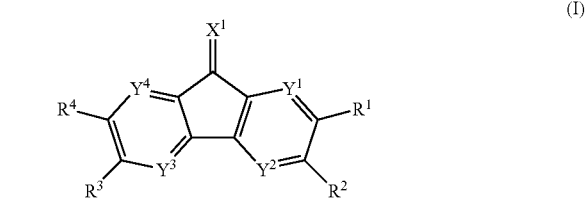

wherein $X^1$ is one of divalent groups represented by the following (a) to (e); $Y^1$ to $Y^4$ are independently a carbon atom or a nitrogen atom; and $R^1$ to $R^4$ are independently a hydrogen atom, an alkyl group, a substituted or unsubstituted aryl group, a substituted or unsubstituted heterocycle, a halogen atom, a fluoroalkyl group or a cyano group, or $R^1$ and $R^2$, and $R^3$ and $R^4$ are independently bonded to form a substituted or unsubstituted aromatic ring or a substituted or unsubstituted heterocycle:

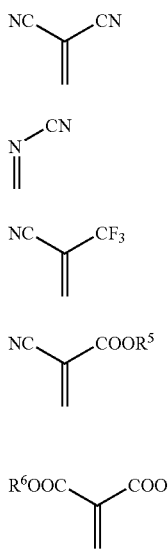

wherein $R^5$ to $R^7$ are independently a hydrogen atom, a fluoroalkyl group, an alkyl group, an aryl group or a heterocyclic group; and $R^6$ and $R^7$ may form a ring.

2. The material for an organic electroluminescence device according to 1, which is a hole-injecting material.

3. The material for an organic electroluminescence device according to 1 or 2, which is a compound represented by the following formula (II):

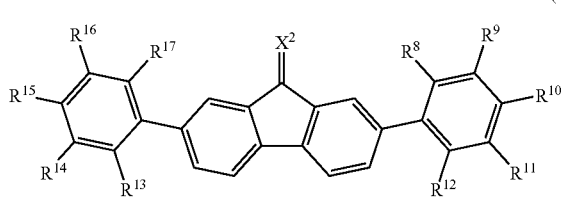

wherein $X^2$ is a divalent group represented by the following (a) or (b); and $R^8$ to $R^{17}$ is independently a hydrogen atom, an alkyl group, an aryl group, a heterocycle, a halogen atom, a fluoroalkyl group or a cyano group.

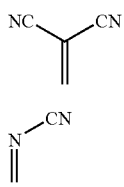

4. The material for an organic electroluminescence device according to 1 or 2, which is a compound represented by the following formula (III):

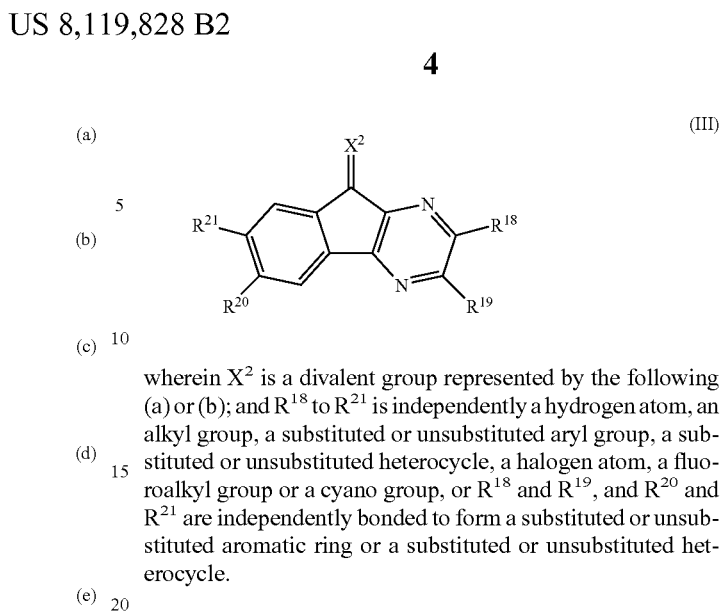

wherein $X^2$ is a divalent group represented by the following (a) or (b); and $R^{18}$ to $R^{21}$ is independently a hydrogen atom, an alkyl group, a substituted or unsubstituted aryl group, a substituted or unsubstituted heterocycle, a halogen atom, a fluoroalkyl group or a cyano group, or $R^{18}$ and $R^{19}$, and $R^{20}$ and $R^{21}$ are independently bonded to form a substituted or unsubstituted aromatic ring or a substituted or unsubstituted heterocycle.

5. The material for an organic electroluminescence device according to any one of 1 to 4, of which the reductive potential in acetonitrile is −1.0V and more (vs Fc⁺/Fc wherein Fc shows ferrocene).

6. An organic electroluminescence device comprising:
  an anode and a cathode; and
  one or plural organic thin film layers provided between the anode and the cathode, the organic thin film layers comprising an emitting layer;
  wherein at least one layer of the organic thin film layers comprises the material for an organic electroluminescence device according to any one of 1 to 5.

7. The organic electroluminescence device according to 6, wherein the organic thin film layers are a multilayer stack comprising a hole-transporting layer, an emitting layer and an electron-transporting layer in this order from the anode.

8. The organic electroluminescence device according to 7, wherein the hole-transporting layer comprises the material for an organic electroluminescence device according to any one of 1 to 5.

9. The organic electroluminescence device according to 6, wherein the organic thin film layers are a multilayer stack comprising a hole-injecting layer, a hole-transporting layer, an emitting layer and an electron-transporting layer in this order from the anode; and
  the hole-injecting layer comprises the material for an organic electroluminescence device according to any one of 1 to 5.

10. The organic electroluminescence device according to 8 or 9, wherein the hole-transporting layer or the hole-injecting layer containing the material for an organic electroluminescence device further comprises a phenylenediamine compound represented by the following formula (IV);

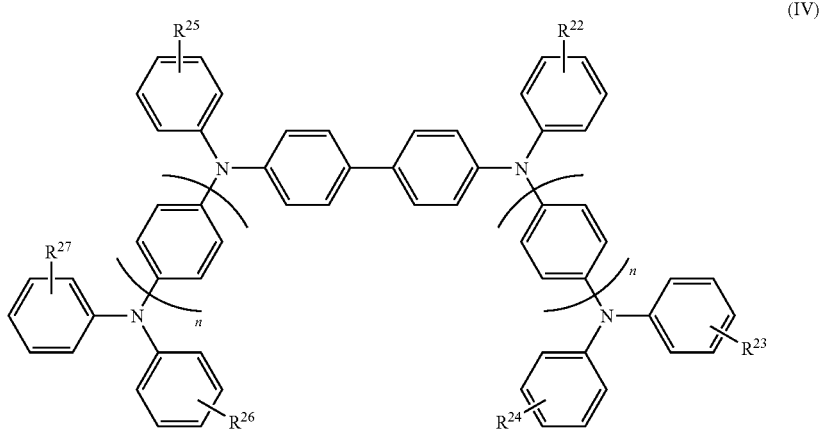

(IV)

wherein $R^{22}$ to $R^{27}$ are independently a hydrogen atom, a halogen atom, a trifluoromethyl group, an alkyl group, an aryl group or a heterocycle, and $R^{22}$ to $R^{27}$ may form a naphthalene skeleton, a carbazole skeleton or a fluorene skeleton with a phenyl group bonded thereto; and n is 1 or 2.

The invention can provide a novel material for an organic EL device. The invention can also provide an organic EL device which can be driven at a lower voltage and has a long life.

BRIEF DESCRIPTION OF THE DRAWINGS

FIG. 1 is a schematic cross-sectional view showing one embodiment of an organic EL device of the invention.

BEST MODE FOR CARRYING OUT THE INVENTION

The material for an organic EL device of the invention will be explained first.

The material for an organic EL device of the present invention is a compound which is represented by the following formula (I):

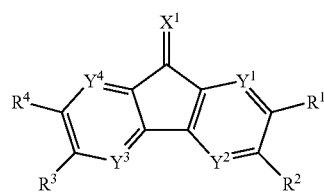

(I)

wherein $X^1$ is one of divalent groups represented by the following (a) to (e); $Y^1$ to $Y^4$ are independently a carbon atom or a nitrogen atom; and $R^1$ to $R^4$ are independently a hydrogen atom, an alkyl group, a substituted or unsubstituted aryl group, a substituted or unsubstituted heterocycle, a halogen atom, a fluoroalkyl group or a cyano group, or $R^1$ and $R^2$, and $R^3$ and $R^4$ are independently bonded to form a substituted or unsubstituted aromatic ring or a substituted or unsubstituted heterocycle:

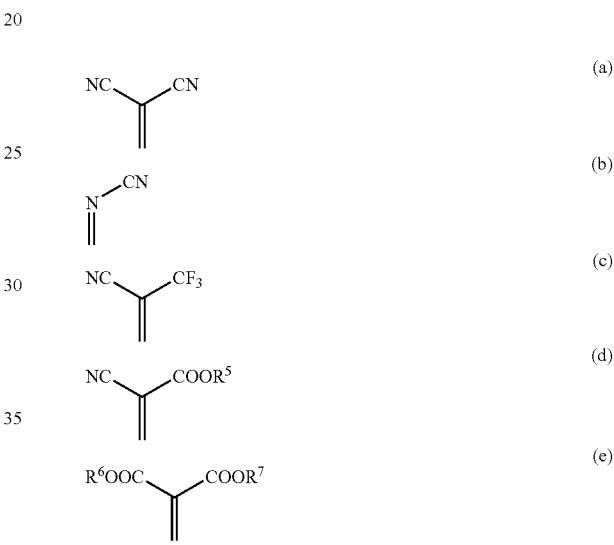

wherein $R^5$ to $R^7$ are independently a hydrogen atom, a fluoroalkyl group, an alkyl group, an aryl group or a heterocyclic group; and $R^6$ and $R^7$ may form a ring.

By using the compound represented by the formula (I) in an organic EL device, the organic EL device can be driven at a lower voltage and can have a longer life.

Examples of the alkyl group shown by $R^1$ to $R^4$ in the formula (I) include methyl, ethyl, propyl, i-propyl, butyl and tert-butyl.

Of these, methyl and tert-butyl are preferable.

As the aryl group shown by $R^1$ to $R^4$, phenyl, naphthyl or the like can be given, for example.

As the substituent, a halogen such as a fluorine atom, a trifluoromethyl group and a cyano group can be given. A plurality of substituents may be bonded to the aryl group. In this case, the substituents may be the same or different.

Of these, a 4-trifluoromethylphenyl group, a 3-trifluoromethylphenyl group, a 4-trifluoromethyl-3-fluorophenyl group, a 3-trifluoromethyl-4-fluorophenyl group, a 4-fluorophenyl group, a 2,4-difluorophenyl group and a 2,3,4-trifluorophenyl group are preferable.

As the heterocycle shown by $R^1$ to $R^4$, a pyridine ring, a pyradine ring, a furan ring, a thiophene ring, an imidazole ring, a benzimidazole ring or the like can be given.

Of these, a pyridine ring, a furan ring and a thiophene ring are preferable.

As the substituent, a halogen such as a fluorine atom, a trifluoromethyl group, a cyano group, a phenyl group or the like can be given. A plurality of substituents may be bonded to the heterocycle. In this case, the substituents may be the same or different.

As the halogen atom shown by $R^1$ to $R^4$, fluorine is preferable.

As the fluoroalkyl group shown by $R^1$ to $R^4$, a trifluoromethyl group is preferable, for example.

$R^1$ and $R^2$, and $R^3$ and $R^4$ may be bonded to form an aromatic ring or a heterocyclic ring. The aromatic ring or the heterocyclic ring may be substituted. Examples include a benzene ring, a pyrazine ring and a pyridine ring shown by the following formulas (f), (g), (h) or the like.

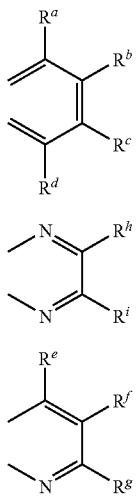

Here, $R^a$ to $R^i$ are a hydrogen atom, a halogen, a cyano group, an alkyl group, a substituted or unsubstituted aryl group, a heterocyclic group, a fluoroalkyl group, an alkoxy group, a substituted or unsubstituted aryloxy group. Specific examples of each substituent are the same as those for $R^1$ in the formula (I). The aryl and the substituent of the substituted or unsubstituted aryloxy group are the same as those of the substituted or unsubstituted aryl group of the formula (I).

Of these, those with the following structure are preferable.

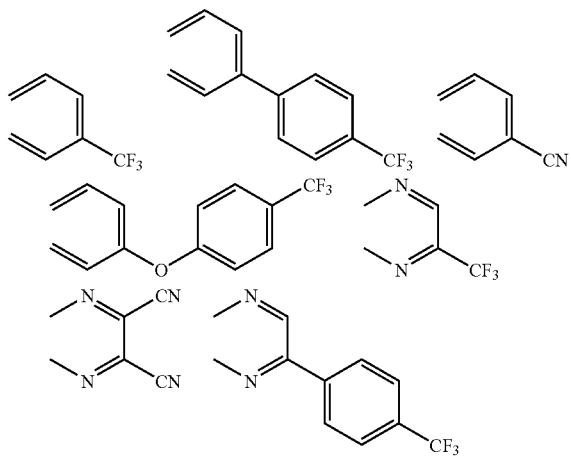

In the above-mentioned divalent substituents (d) and (e), specific examples of the fluoroalkyl group, the alkyl group, the aryl group or the heterocyclic group shown by $R^5$ to $R^7$ are the same as those for $R^1$ to $R^4$.

When the $R^6$ and $R^7$ form a ring, $X^1$ is preferably a substituent shown by the following formula:

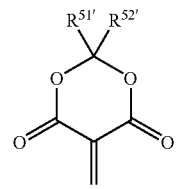

wherein $R^{51'}$ and $R^{52'}$ are each a methyl group, an ethyl group, a propyl group or a tert-butyl group.

Of the compounds shown by the formula (I), compounds shown by the following formula (II) are preferable.

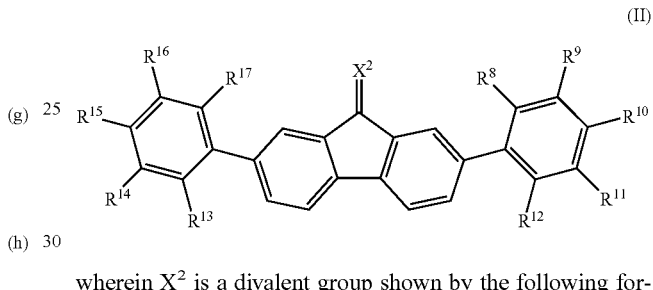

(II)

wherein $X^2$ is a divalent group shown by the following formula (a) or (b), and $R^8$ to $R^{17}$ are each hydrogen, an alkyl group, an aryl group, a heterocycle, a halogen atom, a fluoroalkyl group or a cyano group.

It is preferred that $X^2$ be a divalent group shown by the formula (b) since it improves the purity of the compound due to a lowered sublimation temperature as well as improves heat resistance.

In the formula (II), the specific examples of the alkyl group, the aryl group, the heterocycle, the halogen atom and the fluoroalkyl group shown by $R^8$ to $R^{17}$ are the same as those of $R^1$ to $R^4$.

Of the compounds shown by the formula (I), compounds shown by the following formula (III) are also preferable.

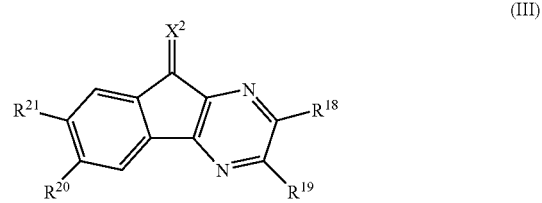

(III)

wherein $X^2$ is the same as those in the formula (II) and $R^{18}$ to $R^{21}$ are the same as those of $R^1$ to $R^4$ in the above formula (I).

It is preferred that the material for an organic EL device of the invention have a reduction potential in an acetonitrile solution of −1.0V (vsFc$^+$/Fc; wherein Fc shows ferrocene) or more (more preferably −0.8V (vsFc$^+$/Fc) or more). Electron acceptability is further increased by using a compound with a reduction potential of −1.0V or more.

The preferred examples of the material for an organic EL device of the invention will be given below.

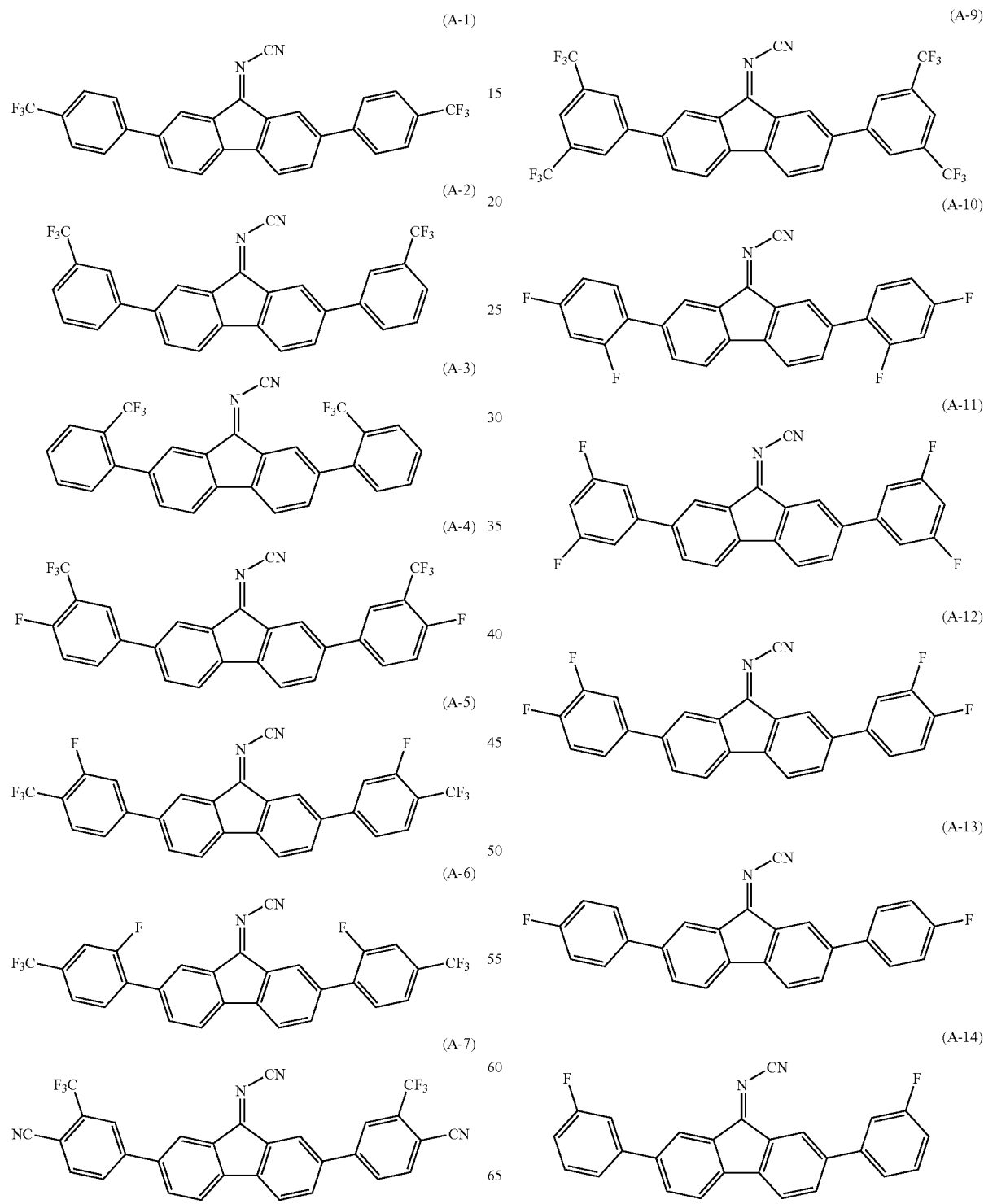

(A-15), (A-16), (A-17), (A-18), (A-19), (A-20), (A-21), (A-22), (A-23), (A-24), (A-25), (A-26), (A-27), (A-28), (A-29)

(A-30) 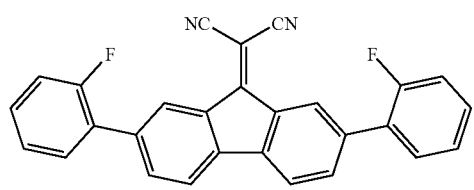
(A-31) 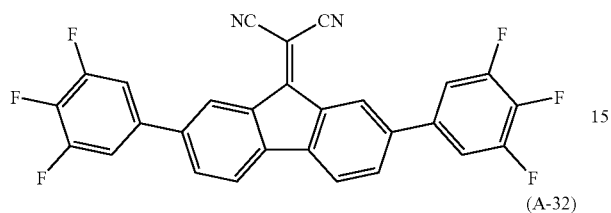
(A-32) 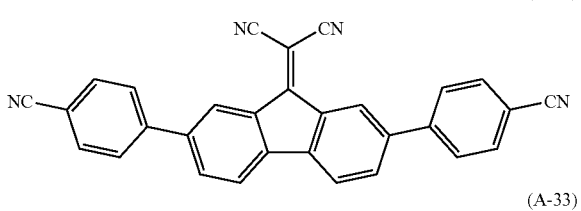
(A-33) 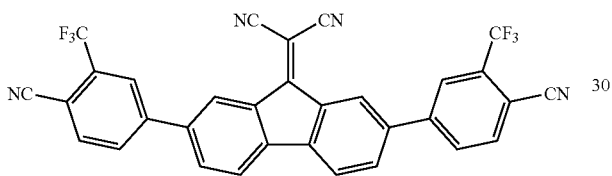
(A-34) 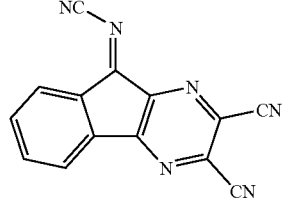
(A-35) 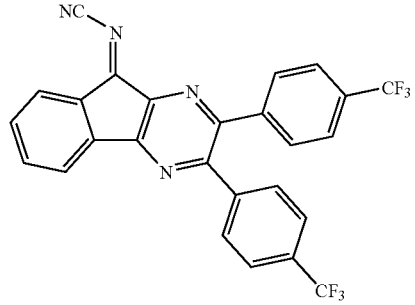
(A-36) 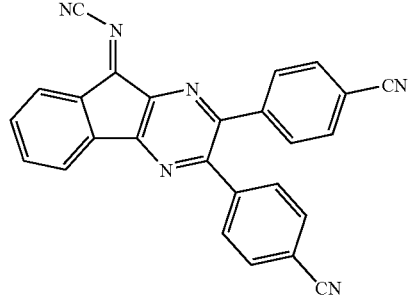
(A-37) 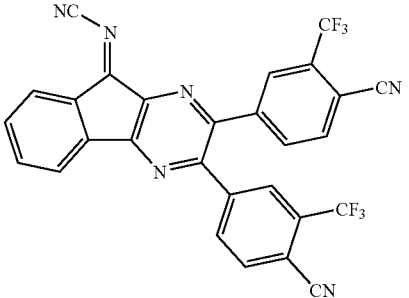
(A-38) 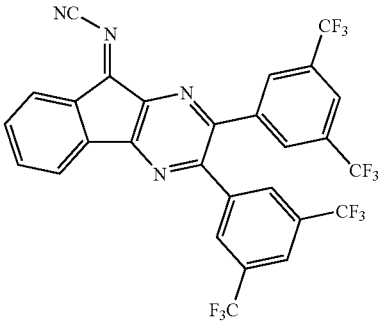
(A-39) 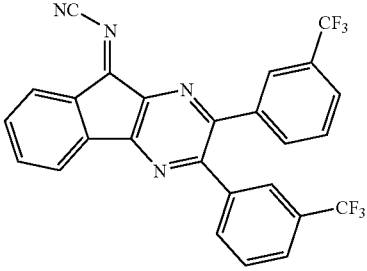
(A-40) 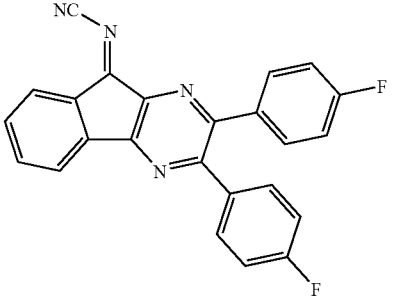
(A-41) 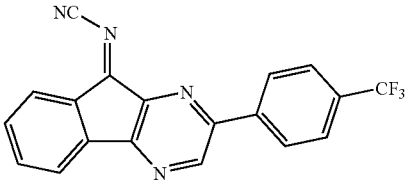

(A-42)
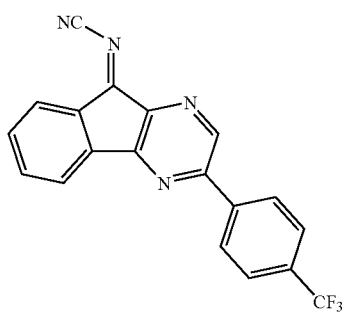
(A-43)
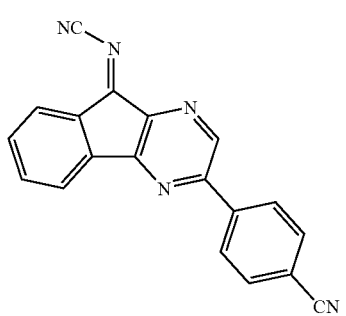
(A-44)
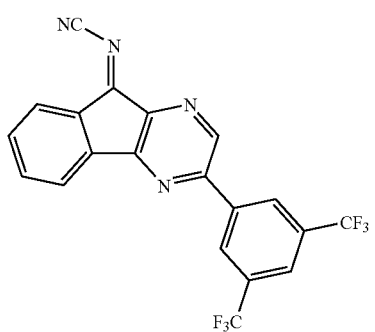
(A-45)
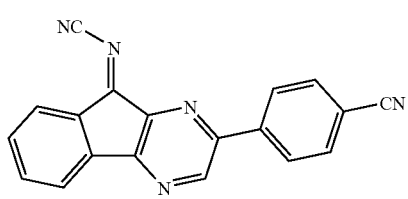
(A-46)
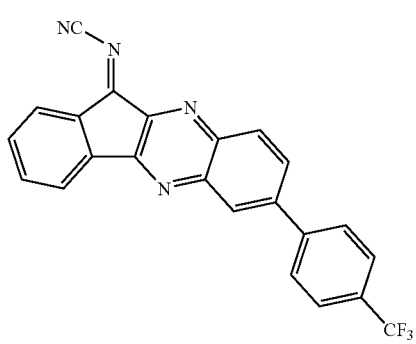
(A-47)
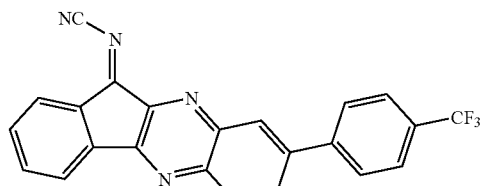
(A-48)
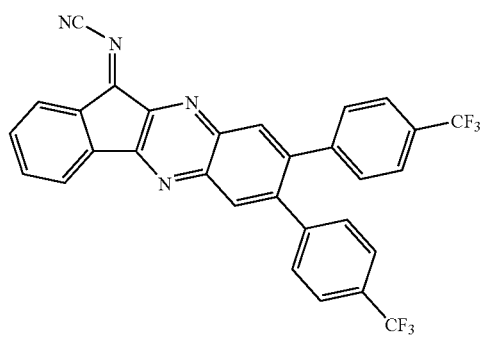
(A-49)
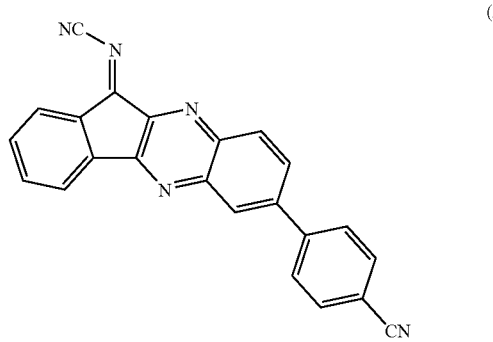
(A-50)
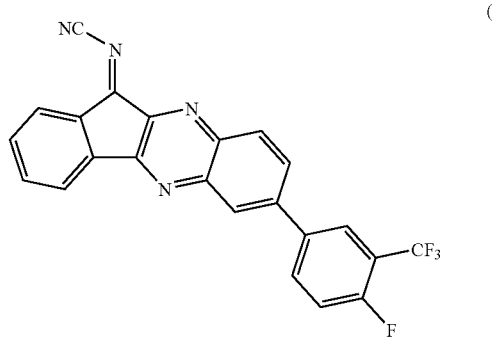
(A-51)
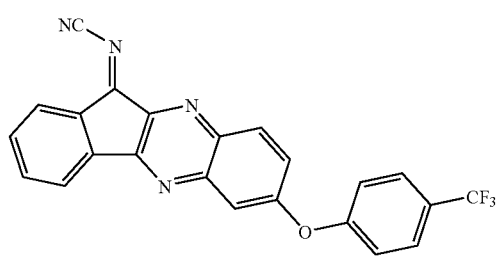

(A-52)
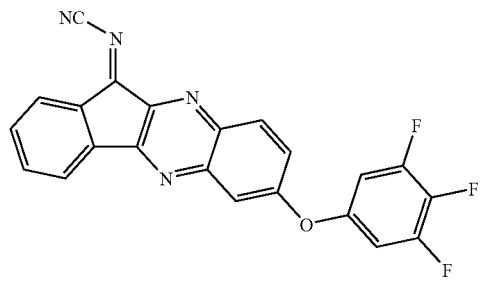
(A-53)
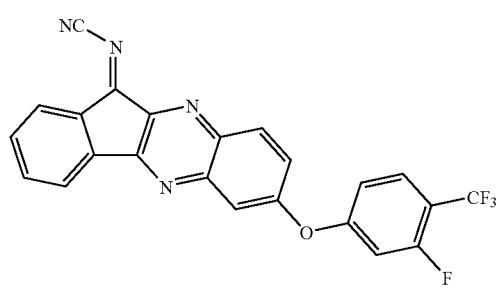
(A-54)
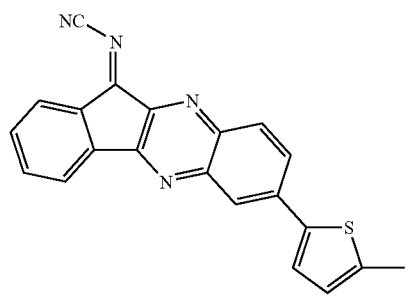
(A-55)
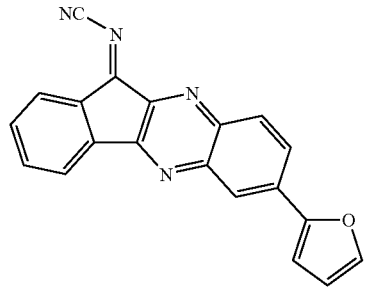
(A-56)
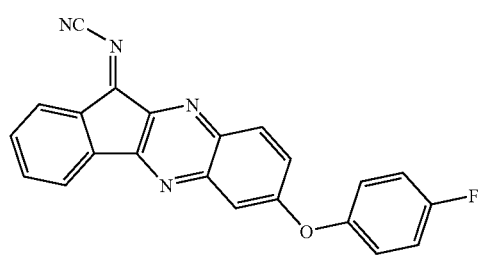
(A-57)
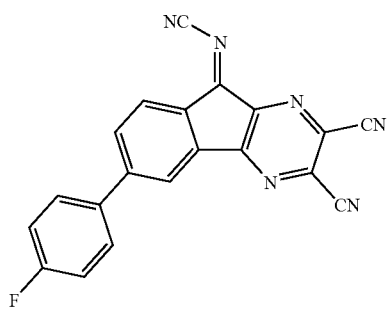
(A-58)
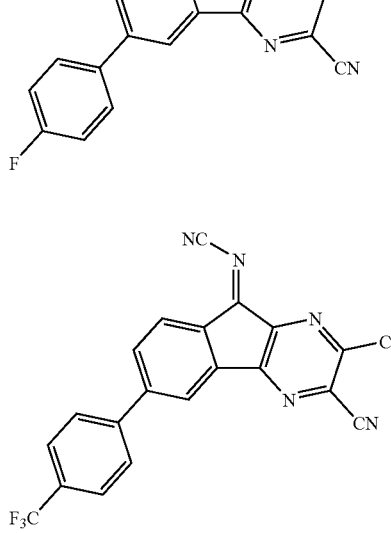
(A-59)
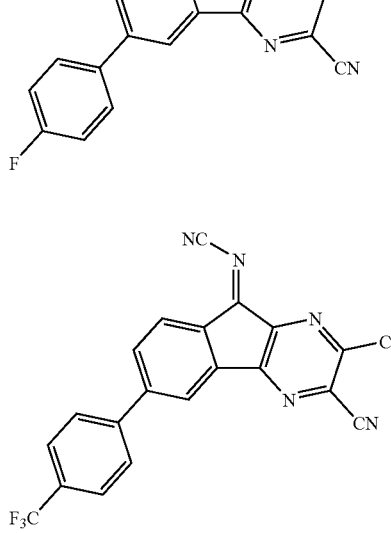
(A-60)
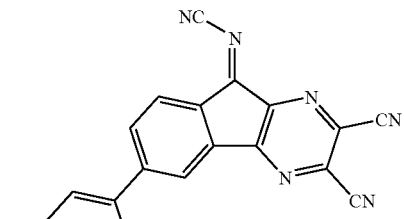
(A-61)
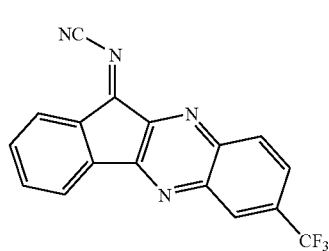

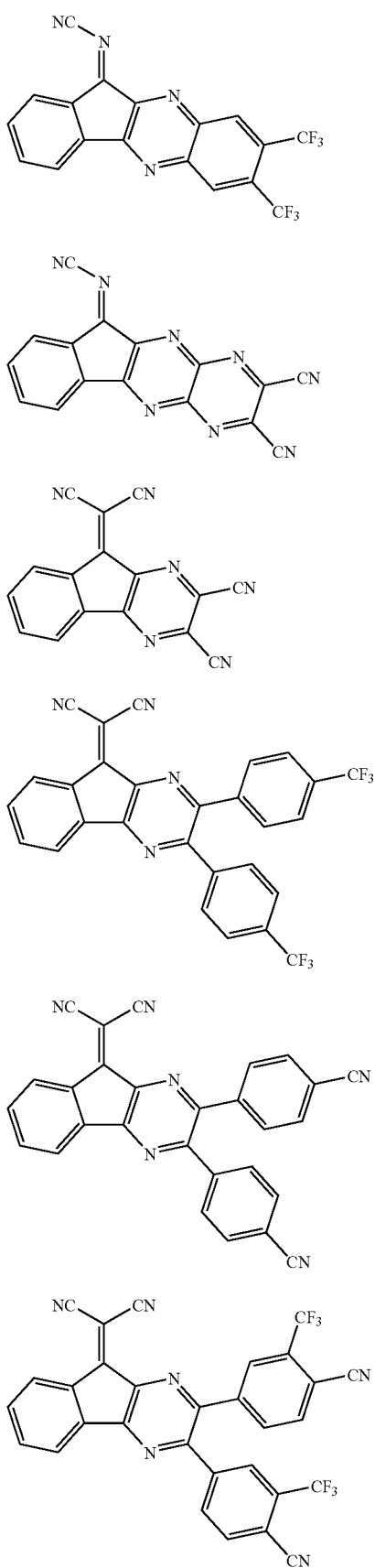

(A-73)
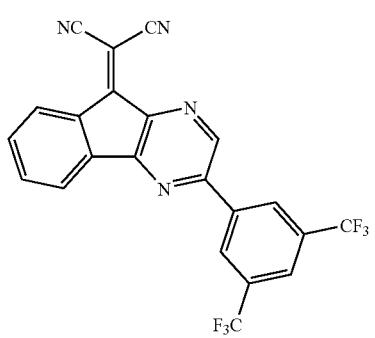
(A-74)
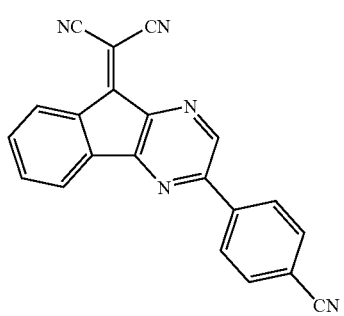
(A-75)
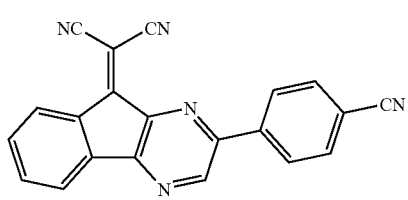
(A-76)
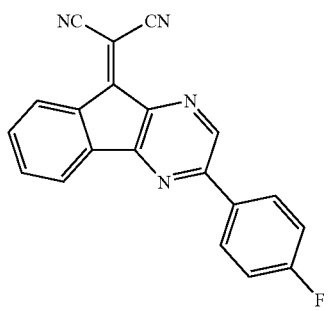
(A-77)
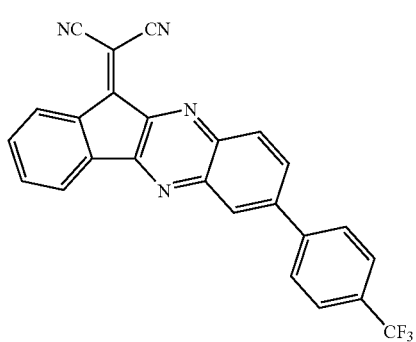
(A-78)
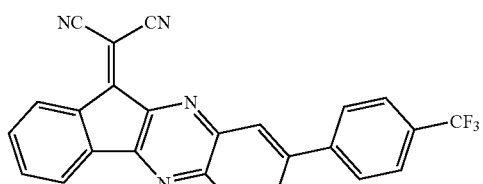
(A-79)
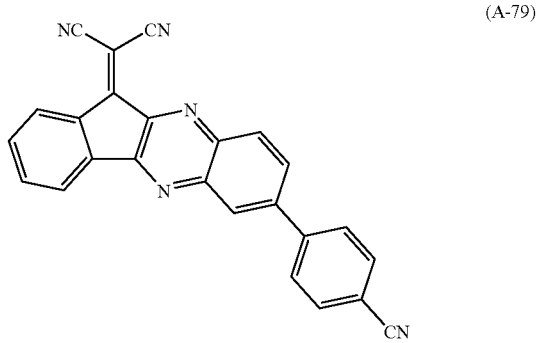
(A-80)
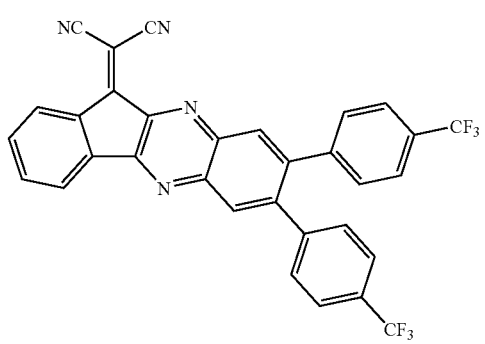
(A-81)
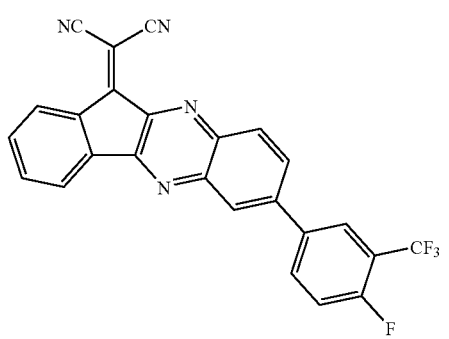
(A-82)
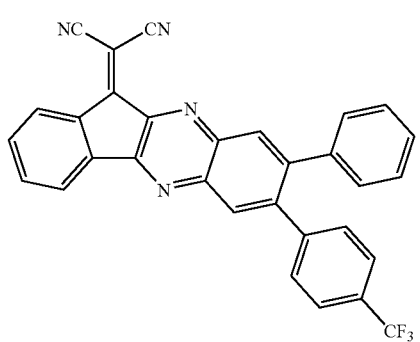

-continued
(A-83)
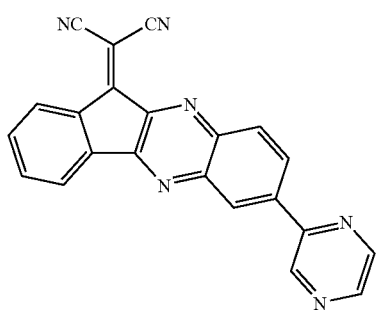
(A-84)
(A-85)
(A-86)
(A-87)
-continued
(A-88)
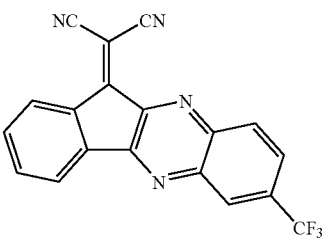
(A-89)
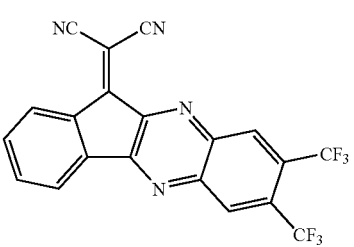
(A-90)
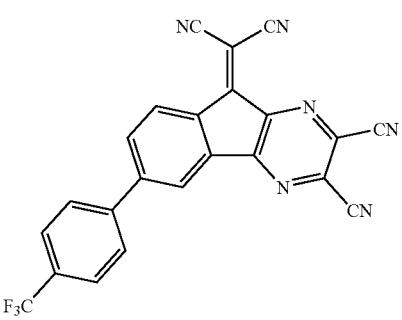
(A-91)
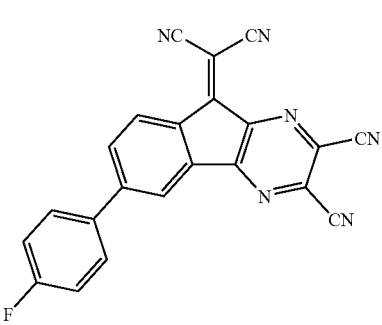
(A-92)
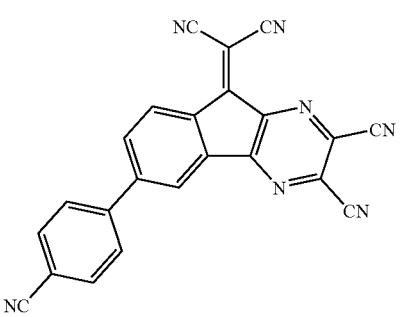

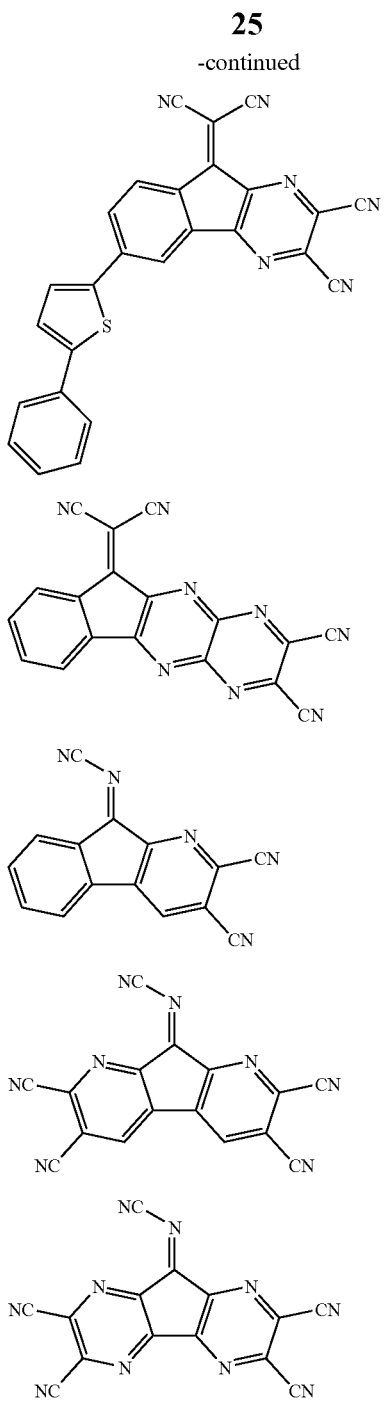
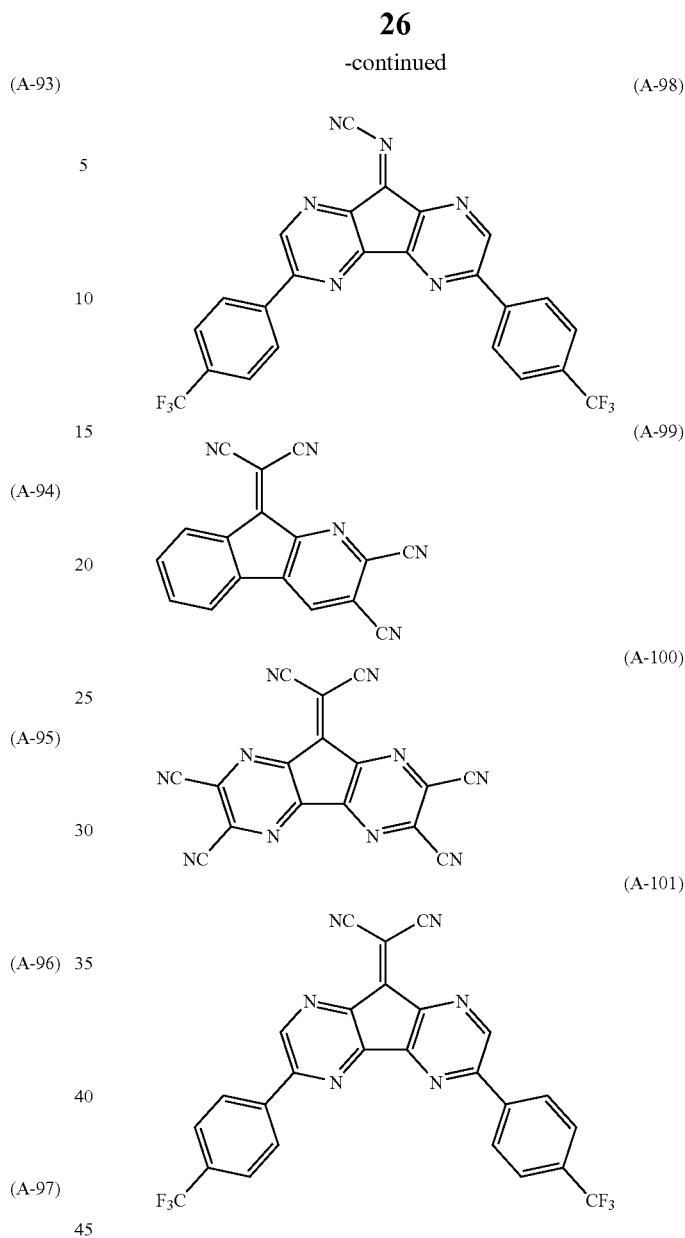
The material for an organic EL device shown by the above formula (I) can be synthesized, for example, by the following scheme 1 or 2. For details such as synthesis conditions, reference can be made to Liebigs Ann. Chem. (1986), page 142 or the like. An intended product is recovered by sublimation and purification.
Scheme 1
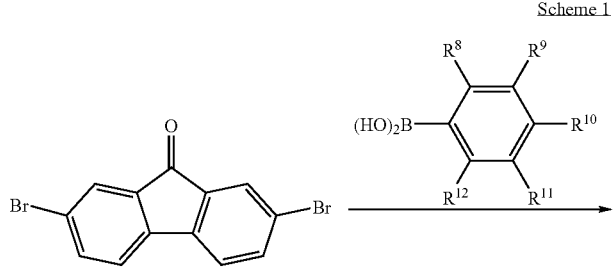

-continued

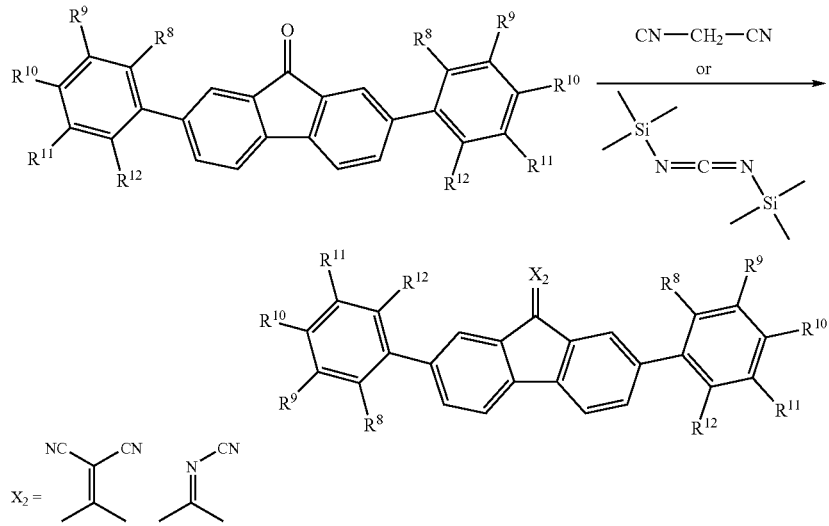

Scheme 2

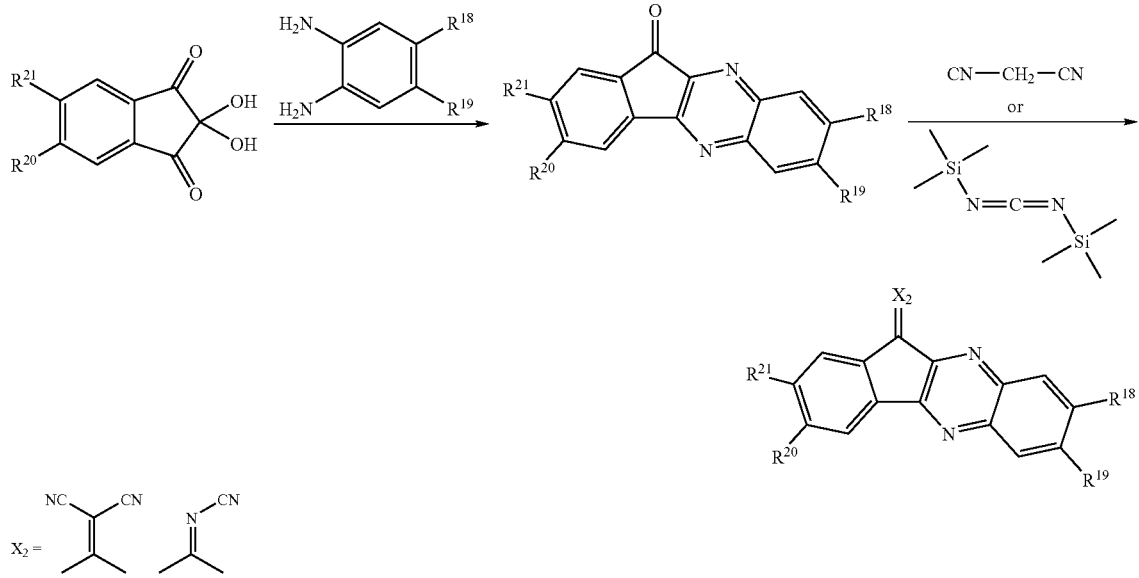

It is preferred that the material for an organic EL device of the invention be used as a hole-injecting material of an organic EL device. Specifically, it is preferable to use it as the material for a layer in a hole-transporting region (in a region between the anode and the emitting layer). By using the material for an organic EL device of the invention as the material for a layer in a hole-transporting region, driving voltage can be lowered and device life can be prolonged.

Next, the organic EL device of the invention will be explained.

The organic EL device of the invention may comprise one or a plurality of organic thin film layers including an emitting layer between the anode and the cathode. At least one layer of the organic thin film layers contains the material for an organic EL device of the invention.

FIG. 1 is a schematic cross-sectional view showing one embodiment of the organic EL device of the invention.

In an organic EL device 1, an anode 10, a hole-injecting layer 20, a hole-transporting layer 30, an emitting layer 40, an electron-transporting layer 50, and a cathode 60 are stacked on a substrate (not shown) in this order. In this device, the organic thin film layer has a stacked structure of the hole-injecting layer 20, the hole-transporting layer 30, the emitting layer 40, and the electron-transporting layer 50. Of these layers forming the organic thin film layer, at least one layer contains the material for an organic EL device of the invention. Due to the presence of the material for an organic EL device of the invention, an organic EL device can have a lowered driving voltage and a longer device life.

The content of the material for an organic EL device of the invention in the layers forming the organic thin film layer is preferably 1 to 100 mol %.

In the organic EL device of the invention, the layer in the region between the anode 10 and the emitting layer 40 (hole-transporting region), specifically the hole-injecting layer 20 or the hole-transporting layer 30, preferably contains the material for an organic EL device of the invention. If the device has both the hole-injecting layer 20 and the hole-transporting layer 30 as in this embodiment, it is preferred that the hole-injecting layer 20 nearer to the anode contain the above-mentioned material.

If the material for an organic EL device of the invention is used in a layer in the hole-transporting region, this material may form the hole-injecting layer or the hole-transporting layer singly or in combination with other materials.

For example, when the material for an organic EL device of the invention is mixed with an aromatic amine derivative to form a hole-injecting layer or a hole-transporting layer, a phenylenediamine compound shown by the formula (IV) is preferable.

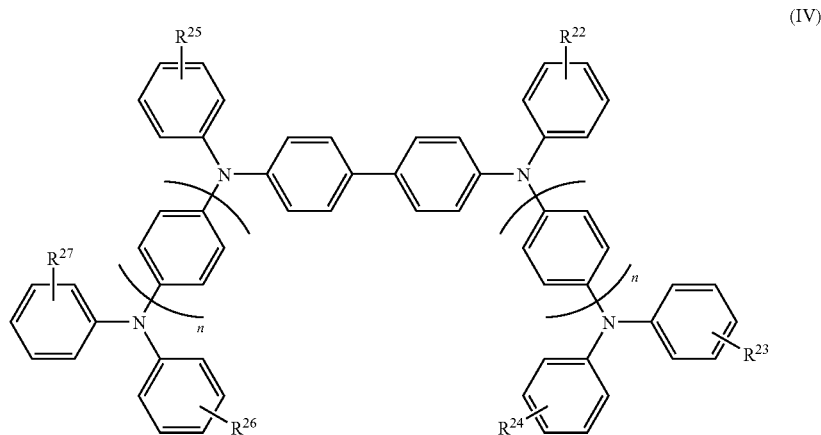

(IV)

wherein $R^{22}$ to $R^{27}$ are hydrogen, a halogen atom, a trifluoromethyl group, an alkyl group, an aryl group, or a heterocycle; $R^{22}$ to $R^{27}$ may form a naphthalene skeleton, a carbazole skeleton, or a fluorene skeleton with a phenyl group bonded thereto; and n is 1 or 2.

If the above phenylenediamine compound is contained in combination, uniformity, heat resistance, or carrier-injection properties of the film may be improved as compared with a case where the material of the invention is contained singly.

In the formula (IV), the fluorine atom is preferable as the halogen atom shown by $R^{22}$ to $R^{27}$.

As the alkyl group shown by $R^{22}$ to $R^{27}$, methyl, isopropyl, tert-butyl and cyclohexyl are preferable.

As the aryl group shown by $R^{22}$ to $R^{27}$, phenyl, naphthyl and fluorenyl are preferable. They may be substituted by a methyl group or the like.

As the heterocycle shown by $R^{22}$ to $R^{27}$, a pyridine ring or a pyrazine ring are preferable.

$R^{22}$ to $R^{27}$ may form a naphthalene skeleton, a carbazole skeleton or a fluorene skeleton with a phenyl group bonded thereto. They may be substituted by a methyl group or the like.

The content of the compound represented by the formula (V) in the hole-transporting layer or the hole-injecting layer is preferably 0.1 to 98 mol %.

Preferred examples of the compound (IV) are given below.

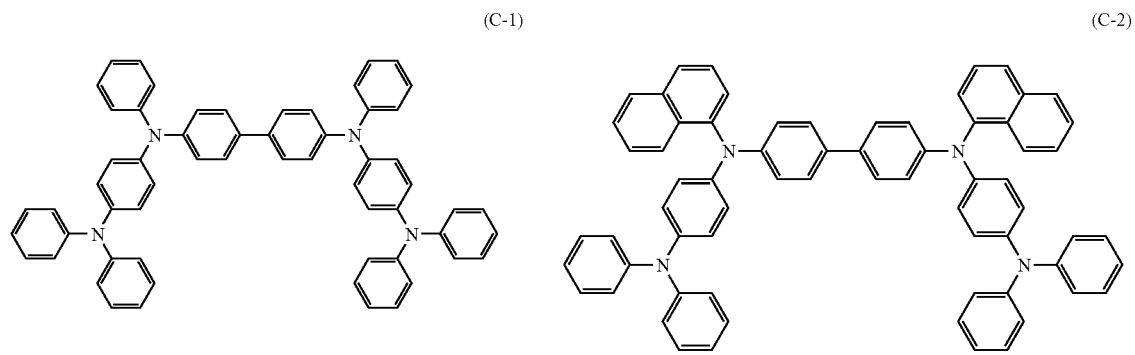

(C-1)    (C-2)

(C-3)
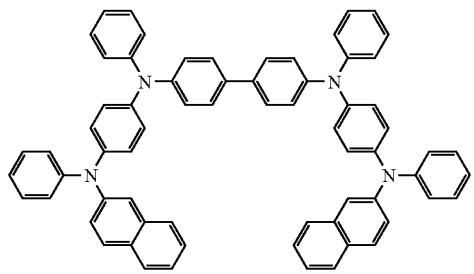
(C-4)
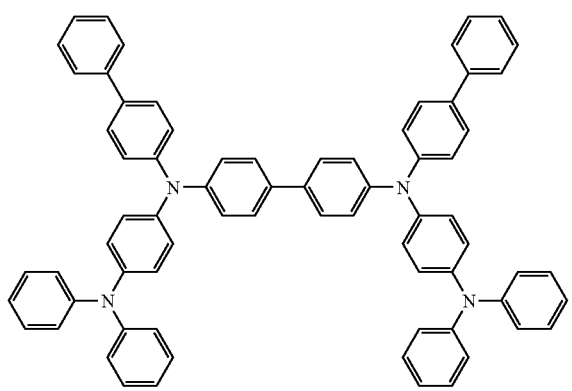
(C-5)
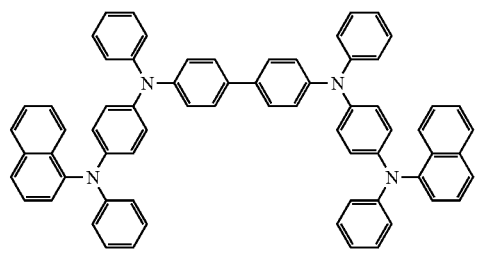
(C-6)
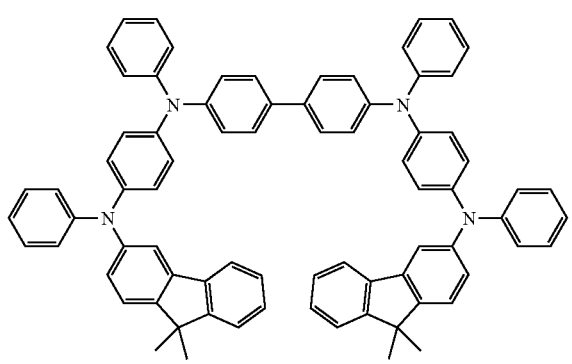
(C-7)
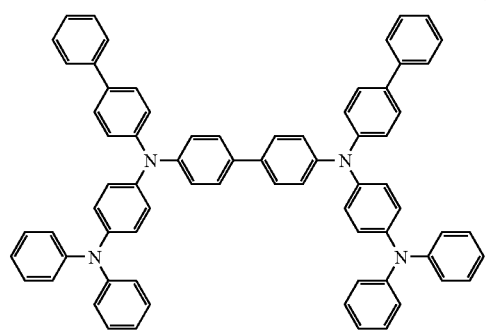
(C-8)
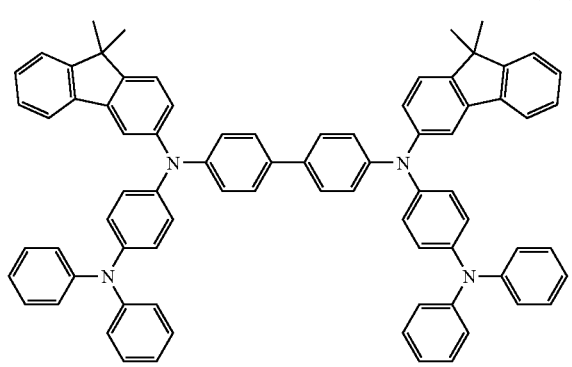

(C-9)
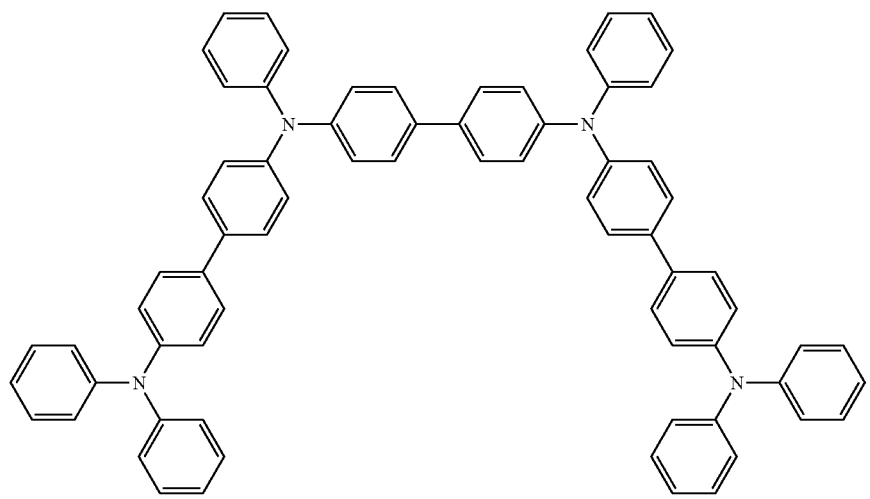
(C-10)
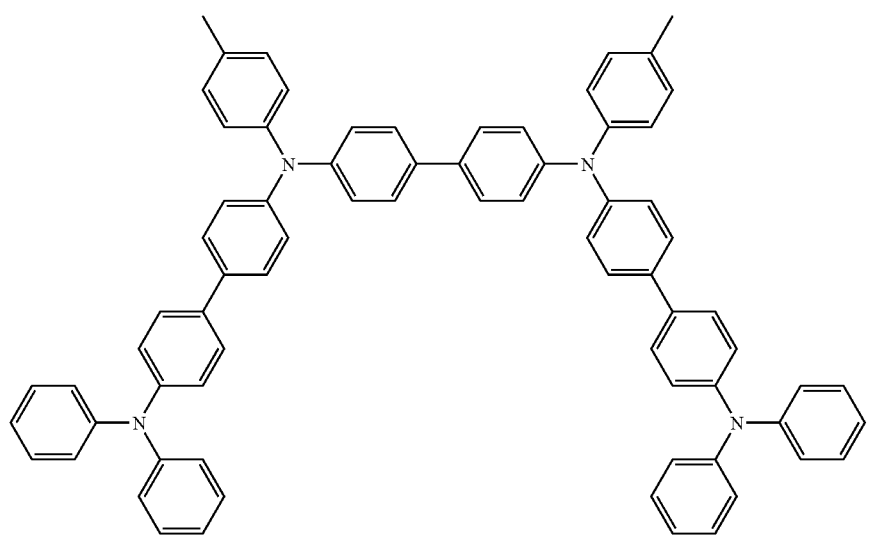
(C-11)
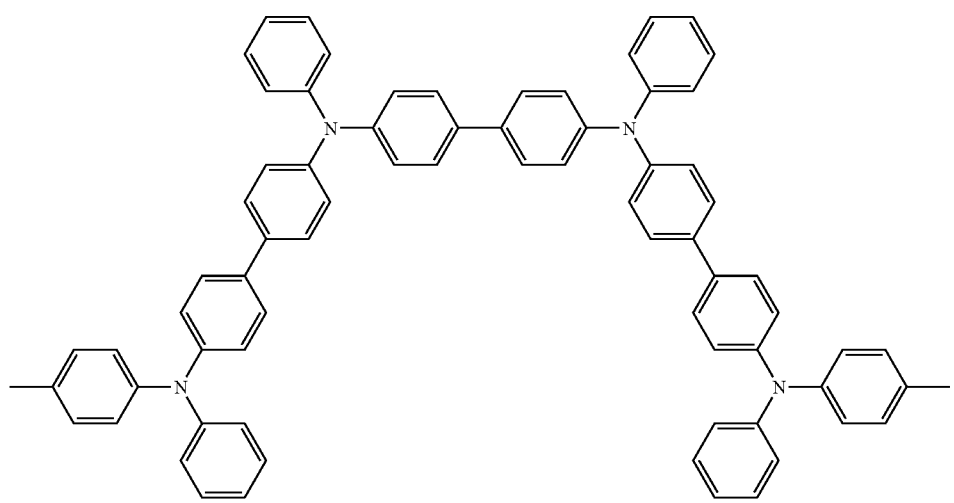

(C-12)

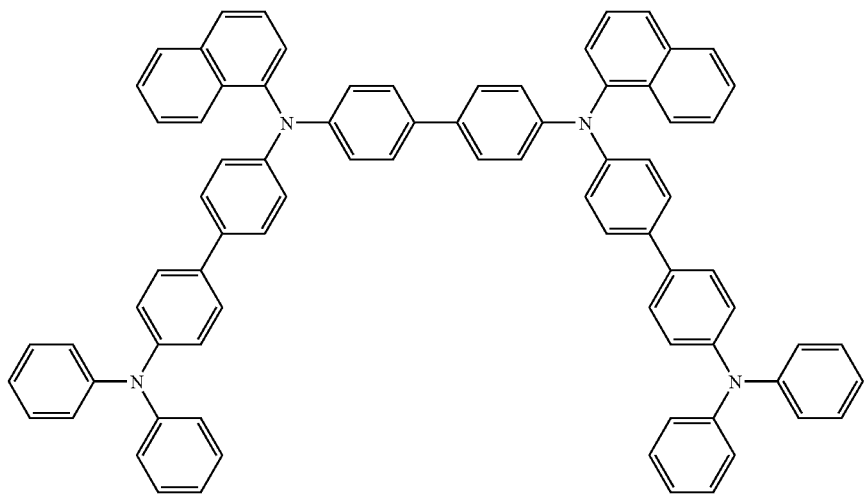

The structure of the organic EL device of the invention is not limited to the embodiment described above, and the organic EL device of the invention may have a structure of (1) to (15) given below.
(1) Anode/emitting layer/cathode
(2) Anode/hole-transporting layer/emitting layer/cathode
(3) Anode/emitting layer/electron-transporting layer/cathode
(4) Anode/hole-transporting layer/emitting layer/electron-transporting layer/cathode
(5) Anode/hole-transporting layer/emitting layer/adhesion-improving layer/cathode
(6) Anode/hole-injecting layer/hole-transporting layer/emitting layer/electron-transporting layer/cathode (FIG. 1)
(7) Anode/hole-transporting layer/emitting layer/electron-transporting layer/electron-injecting layer/cathode
(8) Anode/hole-injecting layer/hole-transporting layer/emitting layer/electron-transporting layer/electron-injecting layer/cathode
(9) Anode/insulating layer/hole-transporting layer/emitting layer/electron-transporting layer/cathode
(10) Anode/hole-transporting layer/emitting layer/electron-transporting layer/insulating layer/cathode
(11) Anode/inorganic semiconductor layer/insulating layer/hole-transporting layer/emitting layer/insulating layer/cathode
(12) Anode/insulating layer/hole-transporting layer/emitting layer/electron-transporting layer/insulating layer/cathode
(13) Anode/hole-injecting layer/hole-transporting layer/emitting layer/electron-transporting layer/insulating layer/cathode
(14) Anode/insulating layer/hole-injecting layer/hole-transporting layer/emitting layer/electron-transporting layer/electron-injecting layer/cathode
(15) Anode/insulating layer/hole-injecting layer/hole-transporting layer/emitting layer/electron-transporting layer/electron-injecting layer/insulating layer/cathode Among these, usually, the structures (4), (6), (7), (8), (12), (13) and (15) are preferably used. Each member constituting the organic EL device of the invention will be described below.
(Transparent Substrate)

The organic EL device is formed on a transparent substrate. The transparent substrate is a substrate for supporting the organic EL device, and is preferably a flat and smooth substrate having a 400-to-700-nm-visible-light transmittance of 50% or more.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Transparency is not required when the supporting substrate is positioned in the direction opposite to the light-outcoupling direction.
(Anode)

The anode of the organic EL device plays a role for injecting holes into its hole-transporting layer or emitting layer. When transparency is required for the anode, indium tin oxide alloy (ITO), tin oxide (NESA), indium zinc oxide alloy (IZO), gold, silver, platinum, copper, and the like may be used as the material for the anode. When a reflective electrode which does not require transparency is used, a metal such as aluminum, molybdenum, chromium, and nickel or alloys thereof may also be used.

Although these materials may be used individually, alloys thereof or materials wherein another element is added to the materials can be appropriately selected for use.

In the case where emission from the emitting layer is taken out through the anode, the transmittance of the anode to the emission is preferably more than 10%. The sheet resistance of the anode is preferably several hundred $\Omega/\square$ or less. The film thickness of the anode, which varies depending upon the material thereof, is usually selected from 10 nm to 1 μm, preferably from 10 to 200 nm.
(Emitting Layer)

The emitting layer of the organic EL device has the following functions (1), (2) and (3) in combination.
(1) Injecting function: function of allowing injection of holes from anode or hole-injecting layer and injection of electrons from cathode or electron-injecting layer upon application of electric field
(2) Transporting function: function of moving injected carriers (electrons and holes) due to the force of an electric field (3) Emitting function: function of allowing electrons and holes to recombine to emit light Note that electrons and holes may be injected into the emitting layer with different degrees, or the transportation capabilities indicated by the mobility of holes and electrons may differ. It is preferable that the emitting layer move either electrons or holes.

As the emitting material or the doping material used for the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bistyryl, pyrazine, cyclopentadiene, a quinoline metal complex, an aminoquinoline metal complex, a benzoquinoline metal complex, imine, diphenyl ethylene, vinylanthracene, diaminocarbazole, pyran, thiopyran, polymethine, merocyanine, an imidazole chelate oxanoid compound, quinacridone, rubrene, a fluorescent pigment and like can be given. Note that the emitting material and the doping material are not limited to these compounds.

As the host material for use in the emitting layer, compounds represented by the following formulas (i) to (ix) are preferred.

Asymmetrical anthracenes represented by the following formula (i)

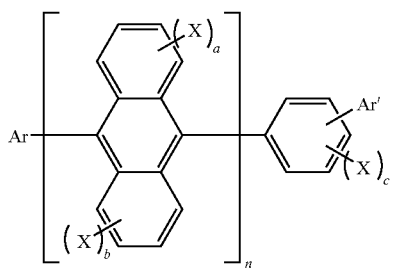

(i)

wherein Ar is a substituted or unsubstituted condensed aromatic group having 10 to 50 atoms for forming a ring (hereinafter referred to as "ring carbon atoms"), Ar' is a substituted or unsubstituted aromatic group having 6 to 50 ring carbon atoms, X' is a substituted or unsubstituted aromatic group having 6 to 50 ring carbon atoms, a substituted or unsubstituted aromatic heterocyclic group having 5 to 50 atoms for forming a ring (hereinafter referred to as "ring atoms"), a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxyl group.

a, b and c are each an integer of 0 to 4.

n is an integer of 1 to 3. When n is two or more, the groups in ▯ may be the same or different.

Asymmetrical monoanthracene derivatives represented by the following formula (ii)

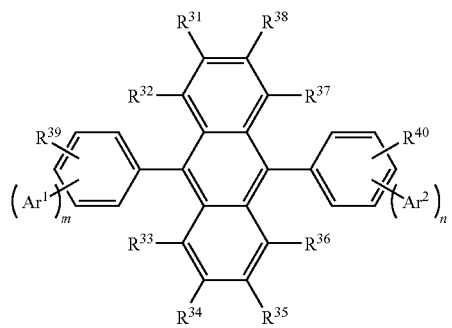

(ii)

wherein $Ar^1$ and $Ar^2$ are independently a substituted or unsubstituted aromatic ring group having 6 to 50 ring carbon atoms, and m and n are each an integer of 1 to 4, provided that in the case where m=n=1 and $Ar^1$ and $Ar^2$ are symmetrically bonded to the benzene rings, $Ar^1$ and $Ar^2$ are not the same, and in the case where m or n is an integer of 2 to 4, m is different from n.

$R^{31}$ to $R^{40}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives represented by the following formula (iii)

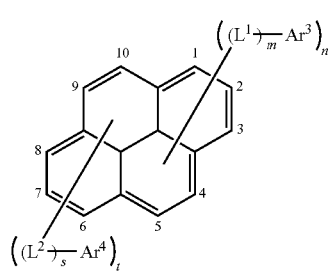

(iii)

wherein $Ar^3$ and $Ar^4$ are independently a substituted or unsubstituted aromatic group having 6 to 50 ring carbon atoms;

$L^1$ and $L^2$ are each a substituted or unsubstituted phenylene group, a substituted or unsubstituted naphthalenylene group, a substituted or unsubstituted fluolenylene group, or a substituted or unsubstituted dibenzosilolylene group;

m is an integer of 0 to 2, n is an integer of 1 to 4, s is an integer of 0 to 2, and t is an integer of 0 to 4;

$L^1$ or $Ar^3$ bonds at any one position of 1 to 5 of the pyrene, and $L^2$ or $Ar^4$ bonds at any one position of 6 to 10 of the pyrene;

provided that when n+t is an even number, $Ar^3$, $Ar^4$, $L^1$ and $L^2$ satisfy the following (1) or (2):

(1) $Ar^3 \neq Ar^4$ and/or $L^1 \neq L^2$ where ≠ means these substituents are groups having different structures from each other, (2) when $Ar^3 = Ar^4$ and $L^1 = L^2$, (2-1) m≠s and/or n≠t, or (2-2) when m=s and n=t, (2-2-1) when $L^1$ and $L^2$ or the pyrene each bond to $Ar^3$ and $Ar^4$ at different positions, or (2-2-2)

when $L^1$ and $L^2$, or the pyrene each bond to $Ar^3$ and $Ar^4$ at the same positions, the pyrene is neither substituted by $L^1$ and $L^2$ or $Ar^3$ and $Ar^4$ at 1 and 6 positions, nor at 2 and 7 positions.

Asymmetrical anthracene derivatives represented by the following formula (iv)

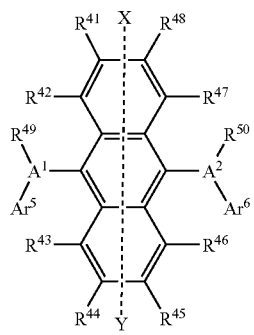

(iv)

wherein $A^1$ and $A^2$ are independently a substituted or unsubstituted condensed aromatic ring group having 10 to 20 ring carbon atoms, $Ar^5$ and $Ar^6$ are independently a hydrogen atom or a substituted or unsubstituted aromatic ring group with 6 to 50 ring carbon atoms, $R^{41}$ to $R^{50}$ are independently a hydrogen atom or a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^5$, $Ar^6$, $R^{49}$ and $R^{50}$ may be plural, and adjacent groups thereof may form a saturated or unsaturated ring structure, provided that groups do not symmetrically bond to 9 and 10 positions of the central anthracene with respect to X-Y axis.

Anthracene derivatives represented by the following formula (v)

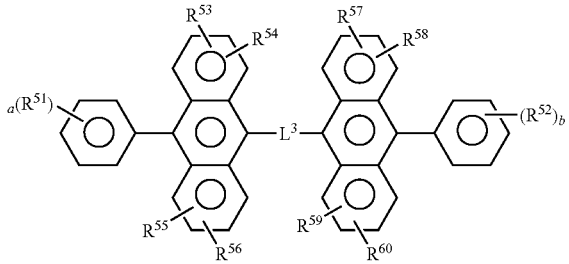

(v)

wherein $R^{51}$ to $R^{60}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are each an integer of 1 to 5; when they are 2 or more, $R^{51}$s or $R^{52}$s may be the same or different, or $R^{51}$s or $R^{52}$s may be bonded together to form a ring; $R^{53}$ and $R^{54}$, $R^{55}$ and $R^{56}$, $R^{57}$ and $R^{58}$, or $R^{59}$ and $R^{60}$ may be bonded together to form a ring; and $L^3$ is a single bond, —O—, —S—, —N(R)— (R is an alkyl group or a substituted or unsubstituted aryl group), an alkylene group or an arylene group.

Anthracene derivatives represented by the following formula (vi)

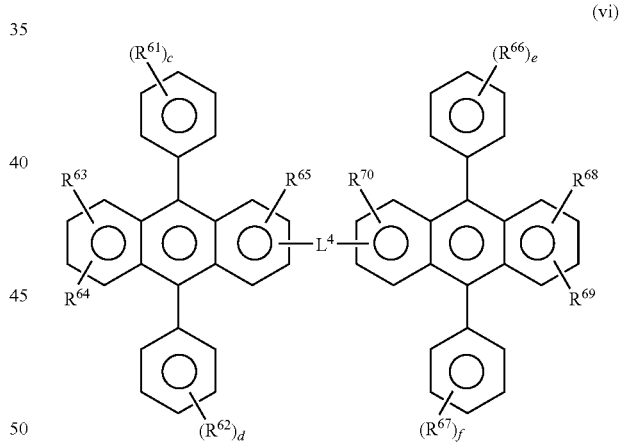

(vi)

wherein $R^{61}$ to $R^{70}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are each an integer of 1 to 5; when they are 2 or more, $R^{61}$s, $R^{62}$s, $R^{66}$s or $R^{67}$s may be the same or different, $R^{61}$s, $R^{62}$s, $R^{66}$s or $R^{67}$s may be bonded together to form a ring, or $R^{63}$ and $R^{64}$, or $R^{68}$ and $R^{69}$ may be bonded together to form a ring; and $L^4$ is a single bond, —O—, —S—, —N(R)— (R is an alkyl group or a substituted or unsubstituted aryl group), an alkylene group or an arylene group.

Spirofluorene derivatives represented by the following formula (vii)

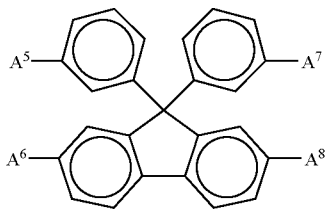

wherein $A^5$ to $A^8$ are each independently a substituted or unsubstituted biphenyl group or a substituted or unsubstituted naphthyl group.

Condensed ring-containing compounds represented by the following formula (viii)

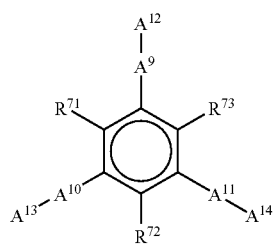

wherein $A^9$ to $A^{14}$ are the same as the above-described ones and $R^{71}$ to $R^{73}$ are independently a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^9$ to $A^{14}$ is a group having a condensed aromatic ring with three or more rings.

Fluorene compounds represented by the following formula (ix)

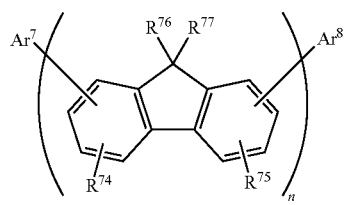

wherein $R^{74}$ and $R^{75}$ are a hydrogen atom, a substituted or unsubstituted alkyl group, substituted or unsubstituted aralkyl group, substituted or unsubstituted aryl group, substituted or unsubstituted heterocyclic group, substituted amino group, cyano group, or a halogen atom. $R^{74}$s or $R^{75}$s bonded to different fluorene groups may be the same or different, and $R^{74}$s and $R^{75}$s bonded to a single fluorene group may be the same or different. $R^{76}$ and $R^{77}$ are a hydrogen atom, a substituted or unsubstituted alkyl group, substituted or unsubstituted aralkyl group, substituted or unsubstituted aryl group, or substituted or unsubstituted heterocyclic group, provided that $R^{76}$s or $R^{77}$s bonded to different fluorene groups may be the same or different, and $R^{76}$ and $R^{77}$ bonded to a single fluorene group may be the same or different. $Ar^7$ and $Ar^8$ are a substituted or unsubstituted condensed polycyclic aromatic group with a total number of benzene rings of three or more or a condensed polycyclic heterocyclic group which is bonded to the fluorene group through substituted or unsubstituted carbon and has a total number of benzene rings and heterocyclic rings of three or more, provided that $Ar^7$ and $Ar^8$ may be the same or different. n is an integer of 1 to 10.

Among the above compounds, the host material is preferably the anthracene derivative, more preferably the monoanthracene derivative, and particularly preferably the asymmetrical anthracene.

Phosphorescent compounds can be used as an emitting material. When using a phosphorescent compound, compounds containing a carbazole ring are preferred for a host material. A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable.

The compounds containing a carbazole ring, which are a host suitable for phosphorescence emission, is a compound which allows a phosphorescent compound to emit as a result of energy transfer from its excited state to the phosphorescent compound. The host compound is not limited so long as the compound can transfer its excitation energy to a phosphorescent compound and it can be selected depending on purposes. The host compound may contain any heterocyclic ring other than a carbazole ring.

Specific examples of the host compounds include carbazole, triazole, oxazole, oxadiazole, imidazole, polyarylalkane, pyrazoline, pyrazolone, phenylenediamine, arylamine, amino-substituted calcone, styryl anthracene, fluorenone, hydrazone, stilbene and silazane derivatives; aromatic tertiary amine, styrylamine, aromatic dimethylidene and porphyrin compounds; anthraquinodimethane, anthrone, diphenylquinone, thiopyrandioxide, carbodiimide, fluoreniridenemethane and distyrylpyrazine derivatives; heterocyclic tetracarboxylic anhydrides such as naphthaleneperylene; phthalocyanine derivatives; metal complexes of 8-quinolinol derivatives; various metal complex polysilane compounds represented by metal complexes having metal-phthalocyanine, benzoxazole or benzothiaole as a ligand; electroconductive macromolecular oligomers such as poly (N-vinylcarbazole) derivatives, aniline copolymers, thiophene oligomers and polythiophene; and polymer compounds such as polythiophene, polyphenylene, polyphenylenevinylene and polyfluorene derivatives. Host compounds can be used individually or as a combination of two or more kinds.

Specific compounds shown below can be exemplified.

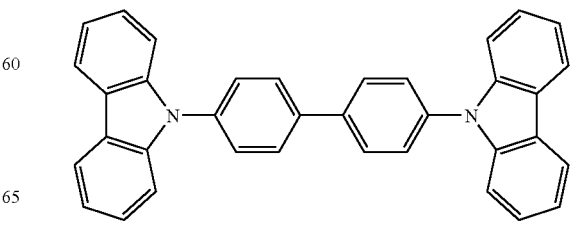

-continued

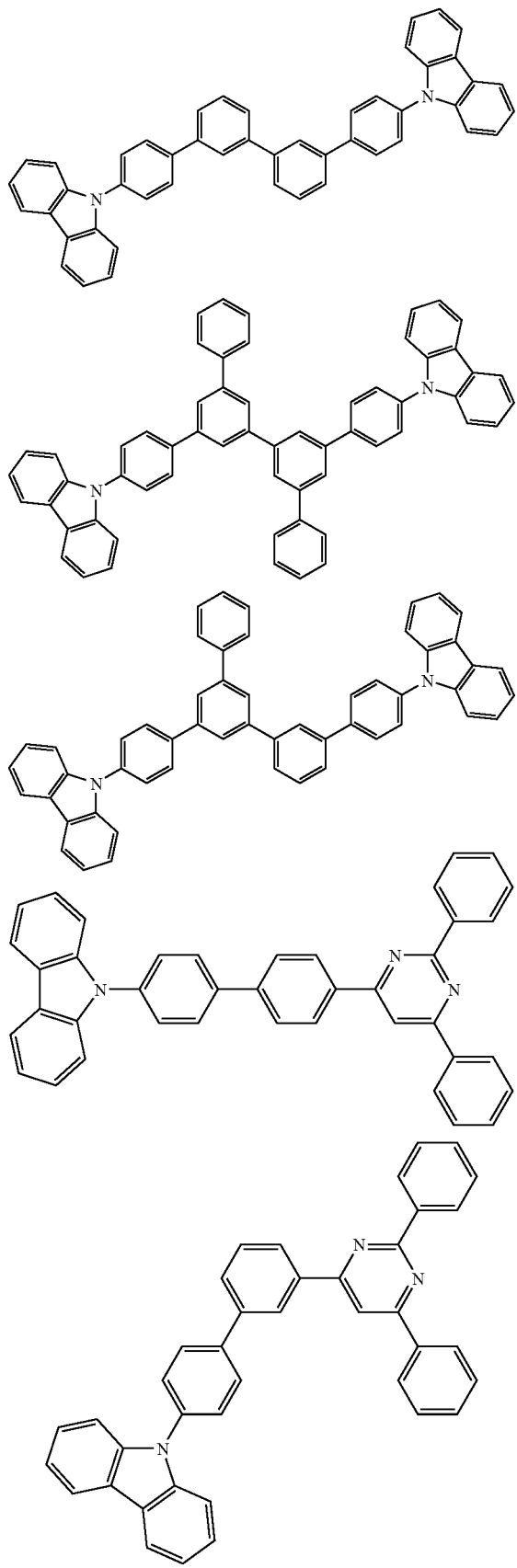

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. As a porphyrin metal complex, a porphyrin platinum complex is preferable. The phosphorescent compounds can be used individually or as a combination of two or more kinds.

There are various ligands forming an ortho-metalated metal complex. Preferable ligands include 2-phenylpyridine, 7,8-benzoquinoline, 2-(2-thienyl)pyridine, 2-(1-naphtyl)pyridine and 2-phenylquinoline derivatives. These derivatives may have substituents, if necessary. Fluorides and derivatives with a trifluoromethyl group introduced are particularly preferable as a blue dopant. As an auxiliary ligand, ligands other than the above-mentioned ligands, such as acetylacetonate and picric acid may be contained.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

(Hole-Transporting:Hole-Injecting Layer)

The hole-transporting layer is a layer for helping the injection of holes into the emitting layer so as to transport holes to an emitting region. The hole mobility thereof is large and the ionization energy thereof is usually as small as 5.5 eV or less. Such a hole-transporting layer is preferably made of a material which can transport holes to the emitting layer at a low electric field intensity. Furthermore, it is preferred that the hole mobility be at least $10^{-4}$ cm$^2$/V·sec when an electric field of $10^4$ to $10^6$ V/cm is applied, for example.

As mentioned above, when using the material for the organic EL device in the hole-transporting region, the compound of the invention may be used singly or in combination with other materials to form a hole-transporting layer. If other materials are mixed, the above-mentioned phenylenediamine compound represented by formula (IV) is preferable.

However, the materials to be mixed are not limited to the compound represented by formula (IV). It is also possible to select appropriately from materials which have been commonly used as a charge-transporting material of holes or known materials used in a hole-injecting layer of an EL device.

If the layers other than those in the hole-transporting region contain the material of the invention, the following materials to be mixed may form the hole-transporting layer singly.

Specific examples of the materials to be mixed include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712 and 47-25336, JP-A-54-53435, 54-110536 and 54-119925, and others), arylamine derivatives (see U.S. Pat. Nos. 3,567,450, 3,180,703, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. Nos. 3,717,462, JP-A-54-59143, 55-52063, 55-52064, 55-46760, 55-85495, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers) disclosed in JP-A-1-211399.

In addition to the hole-transporting layer, it is preferred that a hole-injecting layer be separately provided to help the injection of holes. As the material for the hole-injecting layer, the material for an organic EL device of the invention may be used singly or in combination with other materials. As the other materials, the same materials as the material for the hole-transporting layer may be used. In addition to the compounds represented by the above-mentioned formula (V), porphyrin compounds disclosed in JP-A-63-2956965 and others, aromatic tertiary amine compounds and styrylamine compounds (see U.S. Pat. No. 4,127,412, JP-A-53-27033, 54-58445, 54-149634, 54-64299, 55-79450, 55-144250, 56-119132, 61-295558, 61-98353 and 63-295695, and others) may be used. In particular, aromatic tertiary amine compounds are preferably used.

The following can also be given as examples: 4,4'-bis(N-(1-naphthyl)-N-phenylamino)biphenyl, which has in the molecule thereof two condensed aromatic rings, disclosed in U.S. Pat. No. 5,061,569, and 4,4',4''-tris(N-(3-methylphenyl)-N-phenylamino)triphenylamine, wherein three triphenylamine units are linked to each other in a star-burst form, disclosed in JP-A-4-308688.

Inorganic compounds such as p-type Si and p-type SiC as well as aromatic dimethylidene compounds can also be used as the material of the hole-injecting layer.

The film thickness of the hole-injecting layer and hole-transporting layer is not particularly limited, and is usually from 5 nm to 5 μm. The hole-injecting layer/transporting layer may be a single layer made of one, or two or more of the above-mentioned materials, or may be stacked hole-injecting layers and hole-transporting layers made of different compounds, insofar as the compound of the invention is contained.

An organic semiconductor layer is one type of a hole-transporting layer for helping the injection of holes or electrons into an emitting layer, and is preferably a layer having an electric conductivity of $10^{-10}$ S/cm or more. As the material of such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

(Electron-Injecting/Electron-Transporting Layer)

An electron-injecting layer and an electron-transporting layer are layers which assist injection of electrons into the emission layer so as to transport electrons to an emitting region, and exhibit a high electron mobility. An adhesion-improving layer is one type of the electron-injecting layer formed of a material which exhibits particularly excellent adhesion to the cathode.

The thickness of the electron-injecting layer and the electron-transporting layer is arbitrarily selected in the range of several nanometers to several micrometers. When the electron-transporting layer and the electron-injecting layer have a large thickness, it is preferable that the electron mobility be at least $10^{-5}$ cm$^2$/Vs or more at an applied electric field of $10^4$ to $10^6$ V/cm in order to prevent an increase in voltage.

The material used in the electron-injecting layer and the electron-transporting layer is preferably a metal complex of 8-hydroxyquinoline or a derivative thereof. As specific examples of a metal complex of 8-hydroxyquinoline and the derivative thereof, metal chelate oxinoid compounds including a chelate of oxine (generally, 8-quinolinol or 8-hydroxyquinoline), for example, tris(8-quinolinol)aluminum, can be given.

An electron-transporting compound of the following formula can be given as the oxadiazole derivative.

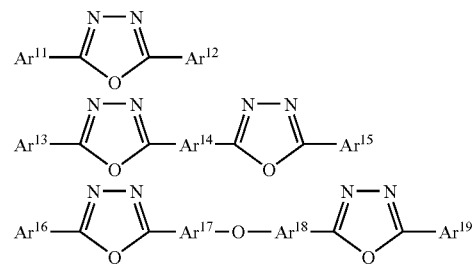

wherein $Ar^{11}$, $Ar^{12}$, $Ar^{13}$, $Ar^{15}$, $Ar^{16}$ and $Ar^{19}$ are independently substituted or unsubstituted aryl groups and may be the same or different. $Ar^{14}$, $Ar^{17}$ and $Ar^{18}$ are independently substituted or unsubstituted arylene groups and may be the same or different.

As examples of the aryl group, a phenyl group, a biphenyl group, an anthryl group, a perylenyl group, and a pyrenyl group can be given. As examples of the arylene group, a phenylene group, a naphthylene group, a biphenylene group, an anthrylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

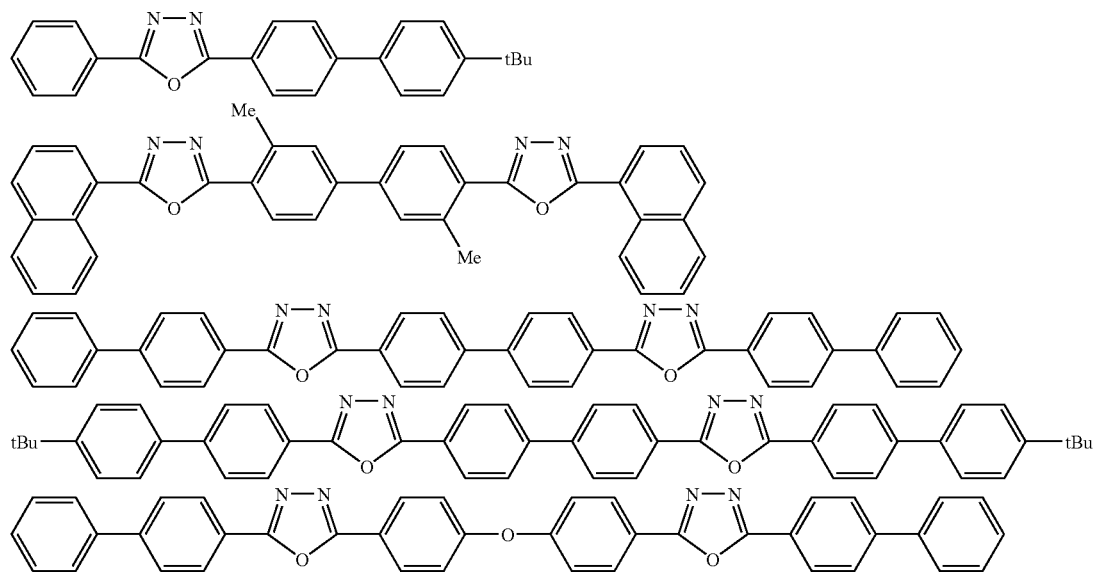

Furthermore, as materials used for the electron-injecting layer and electron-transporting layer, the compounds represented by the following formulas (A) to (F) may also be used.

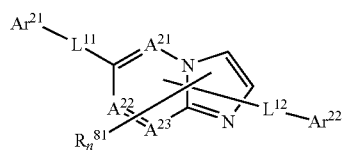

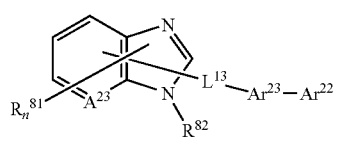

Nitrogen-containing heterocyclic ring derivatives represented by the formulas (A) and (B) wherein $A^{21}$ to $A^{23}$ are each independently a nitrogen atom or a carbon atom;

$Ar^{21}$ is a substituted or unsubstituted aryl group having 6 to 60 ring carbon atoms or a substituted or unsubstituted heteroaryl group having 3 to 60 ring carbon atoms; $Ar^{22}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or a divalent group of these; provided that one of $Ar^{21}$ and $Ar^{22}$ is a substituted or unsubstituted condensed ring group having 10 to 60 ring carbon atoms, a substituted or unsubstituted monohetero condensed ring group having 3 to 60 ring carbon atoms, or a divalent group of these;

$Ar^{23}$ is a substituted or unsubstituted arylene group having 6 to 60 carbon atoms or a substituted or unsubstituted heteroarylene group having 3 to 60 carbon atoms;

$L^{11}$, $L^{12}$ and $L^{13}$ are independently a single bond, a substituted or unsubstituted arylene group having 6 to 60 ring carbon atoms, a substituted or unsubstituted heteroarylene group having 3 to 60 ring carbon atoms or a substituted or unsubstituted fluorenylene group;

$R^{81}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of $R^{81}$s may be the same or different; adjacent $R^{81}$s may be bonded to form a carbocyclic aliphatic ring or a carbocyclic aromatic ring;

$R^{82}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or —$L^{11}$—$Ar^{21}$—$Ar^{22}$.

$$HAr-L^{14}-A^{24}-Ar^{25} \qquad (C)$$

Nitrogen-containing heterocyclic ring derivatives represented by the formula (C) wherein HAr is a nitrogen-containing heterocyclic ring with 3 to 40 carbon atoms which may have a substituent; $L^{14}$ is a single bond, an arylene group with 6 to 60 carbon atoms which may have a substituent, a heteroarylene group with 3 to 60 carbon atoms which may have a substituent or a fluorenylene group which may have a substituent; $Ar^{24}$ is a divalent aromatic hydrocarbon group with 6 to 60 carbon atoms which may have a substituent; and $Ar^{25}$ is an aryl group with 6 to 60 carbon atoms which may have a substituent or a heteroaryl group with 3 to 60 carbon atoms which may have a substituent.

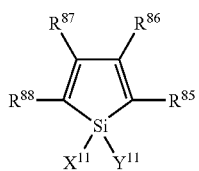
(D)

Silacyclopentadiene derivatives represented by the formula (D) wherein $X^{11}$ and $Y^{11}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or $X^{11}$ and $Y^{11}$ are bonded to form a saturated or unsaturated ring, and $R^{85}$ to $R^{88}$ are independently hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or adjacent groups of $R^{85}$ to $R^{88}$ form a substituted or unsubstituted condensed ring.

(F)

wherein $Q^1$ and $Q^2$ are independently ligands represented by the following formula (G) and $L^{15}$ is a halogen atom, a substituted or unsubstituted alkyl group, a substituted or unsubstituted cycloalkyl group, a substituted or unsubstituted aryl group, a substituted or unsubstituted heterocyclic group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga-$Q^3(Q^4)$ ($Q^3$ and $Q^4$ have the same meanings as $Q^1$ and $Q^2$).

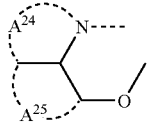
(G)

wherein rings $A^{24}$ and $A^{25}$ are each a 6-membered aryl ring structure which may have a substituent, and are condensed to each other.

The metal complexes have the strong nature of an n-type semiconductor and large ability of injecting electrons. Furthermore, the energy generated at the time of forming a complex is small so that a metal is then strongly bonded to ligands in the complex formed and the fluorescent quantum efficiency becomes large as the emitting material.

Specific examples of the substituents for the rings $A^{24}$ and $A^{25}$ forming the ligand of the formula (G) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino

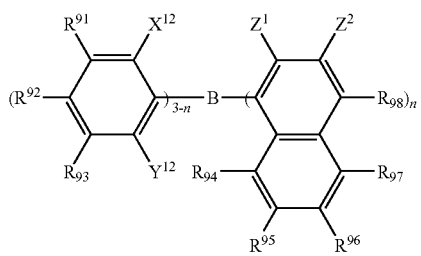
(E)

Borane derivatives represented by the formula (E) wherein $R^{91}$ to $R^{98}$ and $Z^2$ are independently a hydrogen atom, a saturated or unsaturated hydrocarbon group, an aromatic group, a heterocyclic group, a substituted amino group, a substituted boryl group, an alkoxy group, or an aryloxy group, $X^{12}$, $Y^{12}$ and $Z^1$ are independently a saturated or unsaturated hydrocarbon group, an aromatic group, a heterocyclic group, a substituted amino group, an alkoxy group, or an aryloxy group, the substituents for $Z^1$ and $Z^2$ may be bonded to form a condensed ring, n is an integer of 1 to 3, provided that the $Z^1$s may differ when n is 2 or more, and a case in which n is 1, $X^{12}$, $Y^{12}$ and $R^{92}$ are methyl groups, and $R^{98}$ is a hydrogen atom or a substituted boryl group, and a case in which n is 3 and $Z^1$ is a methyl group are excluded.

group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, a carbamoyl group, substituted or substituted carbamoyl groups such as a methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, aryl groups such as a phenyl group, naphthyl group, biphenylyl group, anthryl group, phenanthryl group, fluorenyl group, and pyrenyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triathinyl group, carbazolyl group, furanyl group, thiophenyl group, oxazolyl group, oxadiazolyl group, benzooxazolyl group, thiazolyl group, thiadiazolyl group, benzothiazolyl group, triazolyl group, imidazolyl group, benzimidazolyl group, puranyl group and the like. The above substituents may be bonded to form a further six-membered aryl ring or heterocyclic ring.

A preferred embodiment of the invention is a device containing a reducing dopant in an electron-transferring region or in an interfacial region between the cathode and the organic layer. The reducing dopant is defined as a substance which can reduce an electron-transporting compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Li (work function: 2.9 eV), Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV), which have a work function of 2.9 eV or less.

Among these, a more preferable reducing dopant is at least one alkali metal selected from the group consisting of K, Rb and Cs. Even more preferable is Rb or Cs. Most preferable is Cs.

These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals mentioned above are preferable, particularly combinations including Cs, such as Cs and Na, Cs and K, Cs and Rb, or Cs, Na and K are preferable.

The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, a current leakage can be effectively prevented and electron-injecting properties can be improved.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Semiconductors forming an electron-injecting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn.

An inorganic compound forming an electron-injecting layer is preferably a microcrystalline or amorphous insulating thin film. When the electron-injecting layer is formed of the insulating thin films, more uniformed thin film is formed whereby pixel defects such as a dark spot are decreased.

Examples of such an inorganic compound include the above-mentioned alkali metal calcogenides, alkaline earth metal calcogenides, halides of alkali metals, and halides of alkaline earth metals.

(Cathode)

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where light from the emitting layer is outcoupled through the cathode, the cathode preferably has a light transmittance of larger than 10%.

The sheet resistance of the cathode is preferably several hundred Ω/☐ or less, and the film thickness thereof is usually from 10 nm to 1 μm, preferably from 50 to 200 nm.

(Insulating Layer)

In the organic EL device, pixel defects based on leakage or a short circuit are easily generated since an electric field is applied to the ultrathin film. In order to prevent this, it is preferred to insert an insulative thin film layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, cesium fluoride, cesium carbonate, aluminum nitride, titanium oxide, silicon oxide, germanium oxide, silicon nitride, boron nitride, molybdenum oxide, ruthenium oxide, and vanadium oxide. A mixture or laminate thereof may be used.

(Example of Fabricating an Organic EL Device)

Using the materials as exemplified above, necessary layers are prepared sequentially from an anode, and a cathode is finally formed. The organic EL device can be fabricated in the order reverse to the above, i.e., the order from a cathode to an anode.

An example of the fabrication of the organic EL device will be described below wherein the following layers are successively formed on a transparent substrate: anode/hole-transporting layer/emitting layer/electron-transporting layer/cathode.

First, a thin film made of an anode material is formed into a thickness of 1 μm or less, preferably 10 to 200 nm on an appropriate transparent substrate by vapor deposition, sputtering or some other method, thereby forming an anode.

Next, a hole-transporting layer is formed on this anode. As described above, the hole-transporting layer can be formed by vacuum deposition, spin coating, casting, LB technique, or some other method. Vacuum deposition is preferred since a homogenous film is easily obtained and pinholes are not easily generated.

In the case where the hole-transporting layer is formed by vacuum deposition, conditions for the deposition vary depending upon a compound used (a material for the hole-transporting layer), a desired crystal structure or recombining structure of the hole-transporting layer, and others. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 5 nm to 5 μm.

Next, an emitting layer is formed on the hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-transporting layer.

Next, an electron-transporting layer is formed on this emitting layer. Like the hole-transporting layer and the emitting layer, the layer is preferably formed by vacuum vapor deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vapor deposition or sputtering may be used. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. Specifically, the layers can be formed by a known method, such as vacuum deposition, molecular beam deposition (MBE method), or coating method such as dipping, spin coating, casting, bar coating and roll coating using a solution obtained by dissolving materials in a solvent.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to low efficiency. Usually, the film thickness is preferably in the range of several nanometers to one micrometer.

The organic EL device emits light when applying a voltage between electrodes. If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the cathode and the anode have a positive polarity and a negative polarity, respectively. The waveform of the AC applied may be arbitrary.

EXAMPLES

Synthesis of a Material for an Organic EL Device

In Examples 1 to 5, six kinds of the materials for an organic EL device were prepared.

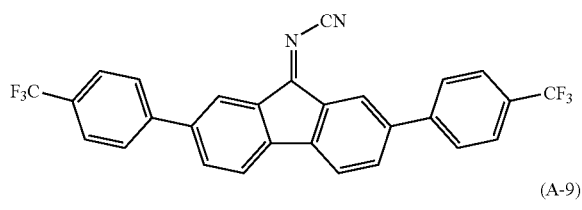
(A-1)

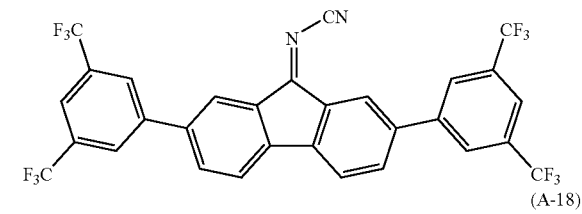
(A-9)

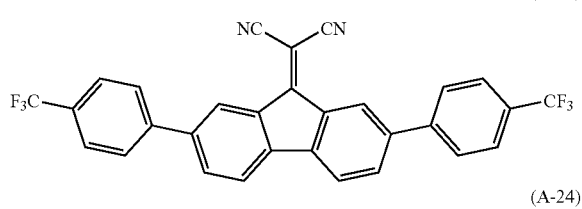
(A-18)

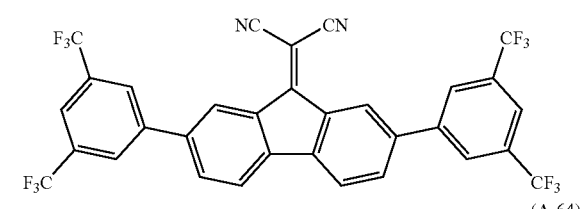
(A-24)

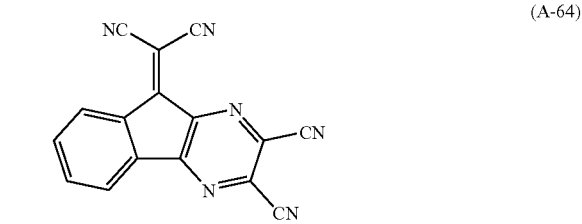
(A-64)

-continued (A-94)

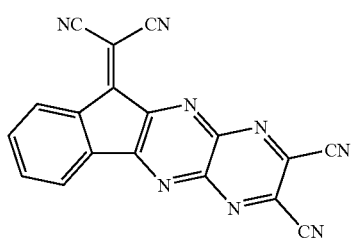

Example 1

Synthesis of A-1

(1) Synthesis of an Intermediate (B-1) Represented by the Following Formula:

(B-1)

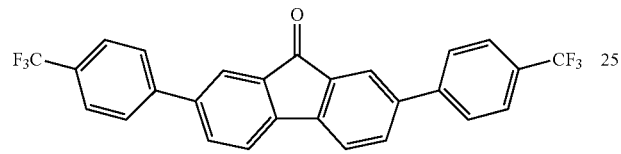

5.0 g of 2,7-dibromo-9-fluorenone, 5.6 g of 4-(trifluoromethyl)phenylboric acid, 5.1 g of potassium fluoride and 0.37 g of tris(dibenzylideneacetone)dipalladium were put in a three-neck flask, and the flask was substituted with argon. Then, 0.26 g of tri-tert-butylphosphine and 40 ml of toluene were added, and the resultant was stirred with heating at 110° C. for 6 hours. After cooling, crystals were filtered, washed with water and methanol, and subjected to column purification with silica gel (chloroform solvent), whereby 1.5 g of a yellow solid was obtained.

Mass spectroscopic measurement of this compound confirmed a peak at M/Z=468.

(2) Synthesis of (A-1)

2.0 g of the B-1 which had been prepared above and 120 ml of methylene chloride were put in a three-neck flask, the flask was substituted with argon. Then, the flask was cooled in a salt-ice bath to 5° C. or lower. Thereafter, a mixed liquid of 10 g of bis(trimethylsilyl)carbodiimide and 20 ml of methylene chloride were added dropwise, and cooled until heat generation is stopped. After cooling, the mixture was stirred under reflux at room temperature for 4 hours. Stirring under reflux was continued for further 2 hours. After cooling, deposited orange crystals were filtered, washed with methanol, and dried. Thereafter, the crystals were purified by sublimation at 220° C., whereby 1.5 g of red-orange crystals were obtained.

As a result of an IR measurement of this compound, absorption of a cyano group was observed at 2186 $cm^{-1}$. Mass spectroscopic measurement confirmed a peak at M/Z=492.

The compound was dissolved in acetonitrile with a concentration of 0.01 mol/l, and the reduction potential thereof was measured by cyclic voltammetry by using tetrabutylammonium perchlorate (TBAP) as a supporting electrolyte and a silver-silver chloride electrode as a reference electrode. The reduction potential of the compound (A-1) with the first oxidation potential of ferrocene (hereinafter referred to as Fc) as a reference material being as the standard is shown in Table 1.

Example 2

Synthesis of A-18

2.0 g of the intermediate (B-1) which had been prepared above, 0.28 g of malononitrile, 30 ml of ethanol and six drops of piperidine were put in a three-neck flask, and the resultant were stirred with heating at 80° C. for 3 hours. After cooling the reaction liquid, deposited crystals were filtered, washed with methanol, and dried under reduced pressure. Thereafter, the crystals were purified by sublimation at 230° C., whereby 1.2 g of purple crystals were obtained.

As a result of an IR measurement of this compound, absorption of a cyano group was observed at 2195 $cm^{-1}$. Mass spectroscopic measurement confirmed a peak at M/Z=516.

In the same manner as in Example 1, the first reduction potential was measured. The results are shown in Table 1.

Example 3

(1) Synthesis of an Intermediate (B-2) Represented by the Following Formula (B-2)

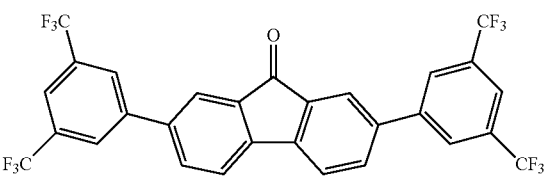

5.0 g of 2,7-dibromo-9-fluorenone, 7.5 g of 3,5-bis(trifluoromethyl)phenylboric acid, 9.2 g of sodium carbonate, 35 g of water and 0.65 g of tetrakis(triphenylphosphine)palladium were put in a three-neck flask, and the flask was substituted with argon. Then, 0.26 g of P(t-Bu)$_3$ and 40 ml of toluene were added, and the resultant was stirred with heating at 110° C. for 6 hours. After cooling, crystals were filtered, washed with water and methanol, and subjected to column purification with silica gel (chloroform solvent), whereby 1.3 g of a yellow solid was obtained. Mass spectroscopic measurement of this compound confirmed a peak at M/Z=604.

(2) Synthesis of (A-9)

The same procedure as in the synthesis of (A-1) of Example 1(2) was repeated, except that 2.0 g of the intermediate (B-1) was changed to 2.5 g of the intermediate (B-2), whereby 1.5 g of pink crystals were obtained.

As a result of an IR measurement of this compound, absorption of a cyano group was observed at 2192 $cm^{-1}$. Mass spectroscopic measurement confirmed a peak at M/Z=628. In the same manner as in Example 1, the first reduction potential of the resulting compound was measured. The results are shown in Table 1.

Example 4

Synthesis of A-24

The same procedure as in the synthesis of (A-18) of Example 2 was repeated, except that 2.0 g of the intermediate (B-1) was changed to 2.5 g of the intermediate (B-2), whereby 1.6 g of pink crystals were obtained.

As a result of an IR measurement of this compound, absorption of a cyano group was observed at 2220 cm$^{-1}$. Mass spectroscopic measurement confirmed a peak at M/Z=652. In the same manner as in Example 1, the first reduction potential of the resulting compound was measured. The results are shown in Table 1.

Example 5

Synthesis of A-64

(1) Synthesis of an Intermediate (B-3) Represented by the Following Formula

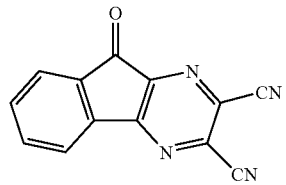

(B-3)

10 g of ninhydrine, 6.3 g of diaminomaleonitrile and 60 ml of ethanol were put in a three-neck flask, and the resultant was stirred under reflux for 1 hour. After cooling to room temperature, deposited yellow crystals were filtered. The crystals were then subjected to column purification with silica gel (developing solvent: methylene chloride), whereby 9.6 g of a yellow solid was obtained. Mass spectroscopic measurement of this compound confirmed a peak at M/Z=232.

(2) Synthesis of (A-64)

5.5 g of the intermediate (B-3) which had been prepared above, 1.6 g of malononitrile, 160 ml of ethanol and ten drops of piperidine were put in a three-neck flask, and the resultant were stirred with heating at 80° C. for 6 hours. After cooling the reaction liquid, deposited crystals were filtered, washed with methanol, and dried under reduced pressure. Thereafter, the crystals were purified by sublimation at 230° C., whereby 2.3 g of orange crystals were obtained.

As a result of an IR measurement of this compound, absorption of a cyano group was observed at 2282 cm$^{-1}$ and 2132 cm$^{-1}$. Mass spectroscopic measurement confirmed a peak at M/Z=280. In the same manner as in Example 1, the first reduction potential of the resulting compound was measured. The results are shown in Table 1.

Example 6

Synthesis of A-94

(1) Synthesis of an Intermediate (B-4) Represented by the Following Formula (B-4)

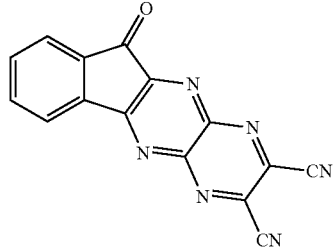

3.6 g of ninhydrine, 3.2 g of 5,6-diamino-2,3-dicyanopyrazine and 100 ml of acetic acid were put in a three-neck flask, and the resultant was stirred under reflux for 8 hours. After cooling to room temperature, deposited yellow crystals were filtered. The crystals were washed with acetonitrile and methanol, and dried, whereby 5.2 g of yellow crystals were obtained. Mass spectroscopic measurement of this compound confirmed a peak at M/Z=284.

(2) Synthesis of (A-94)

4.0 g of the intermediate (B-4) which had been prepared above, 1.5 g of malononitrile and 100 ml of pyridine were put in a three-neck flask, and the resultant were stirred at room temperature for 6 hours under a nitrogen gas atmosphere. Deposited crystals were filtered, washed with dilute hydrochloric acid, ion exchange water and methanol, and dried. Thereafter, the crystals were purified by sublimation at 280° C., whereby 3.2 g of dark red crystals were obtained.

As a result of an IR measurement of this compound, absorption of a cyano group was observed at 2272 cm$^{-1}$ and 2135 cm$^{-1}$. Mass spectroscopic measurement confirmed a peak at M/Z=332. In the same manner as in Example 1, the first reduction potential of the resulting compound was measured. The results are shown in Table 1.

TABLE 1

| Compound | Reduction potential (V vsFc$^+$/Fc) |
| --- | --- |
| A-1 | −0.95 |
| A-18 | −1.00 |
| A-9 | −0.95 |
| A-24 | −1.00 |
| A-64 | −0.46 |
| A-94 | −0.43 |

Fabrication of an Organic EL Device

Example 7

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

The cleaned glass substrate having the transparent electrode lines was then secured to a substrate holder of an apparatus for vacuum deposition. First, the compound represented by the formula (A-1) synthesized in Example 1 and a compound represented by the following formula (C-1) were deposited onto the surface of the glass substrate on which the transparent electrode lines were formed so as to cover the transparent electrodes, thereby forming a 60 nm-thick film in which the compound represented by the formula (A-1) and the compound represented by the following formula (C-1) were mixed at a molar ratio of 2:98. The film of the compound mixture served as a hole-injecting layer.

Subsequently, a 20 nm-thick film of a compound represented by the following formula (HTM-1) was formed on the above-obtained film of the compound mixture. This film functioned as a hole-transporting layer.

Further, EM1 with a thickness of 40 nm was deposited thereon to form a film. Simultaneously, the following amine compound D1 with a styryl group was deposited such that the weight ratio of EM1 and D1 became 40:2. This film functioned as an emitting layer.

A compound (Alq) was deposited to form a 10 nm-thick film on the above-obtained film. The film serves as an electron-injecting layer. Then, Li as a reductive dopant (Li source:

manufactured by SAES Getters Co., Ltd.) and Alq were co-deposited, whereby an Alq:Li film (film thickness: 10 nm) was formed as an electron-injecting layer (cathode). Metal aluminum was deposited on the Alq:Li film to form a metallic cathode, whereby an organic EL emitting device was fabricated.

The organic EL device was evaluated by measuring a driving voltage at a current density of 10 mA/cm$^2$ and a half life of luminance at an initial luminance of 1,000 nits, at room temperature, and with a DC constant power supply. The results obtained are shown in Table 2.

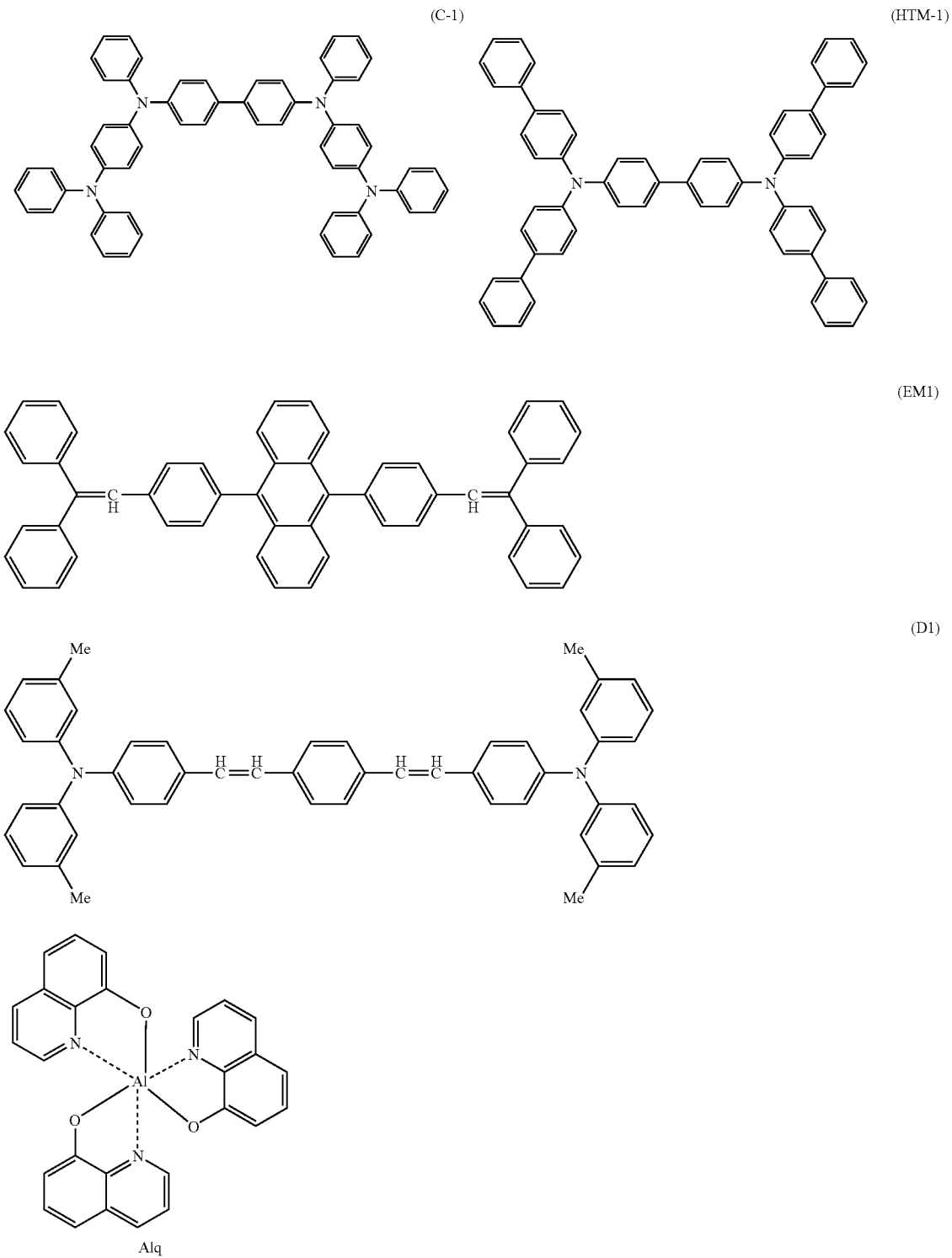

Example 8

An organic EL device was fabricated and evaluated in the same manner as in Example 7, except that the (A-9) synthesized in Example 3 was used singly in the hole-injecting layer. The results are shown in Table 2.

Example 9

An organic EL device was fabricated and evaluated in the same manner as in Example 7, except that the (A-64) synthesized in Example 5 was used singly in the hole-injecting layer. The results are shown in Table 2.

Example 10

An organic EL device was fabricated and evaluated in the same manner as in Example 7, except that the (A-94) synthesized in Example 6 was used singly in the hole-injecting layer, the thickness of the hole-injecting layer was changed to 10 nm and the thickness of the (HTM-1) as the hole-transporting layer was changed to 70 nm. The results are shown in Table 1.

Comparative Example 1

An organic EL device was fabricated and evaluated in the same manner as in Example 7, except that the compound represented by formula (C-1) was used singly for forming the hole-injecting layer. The results are shown in Table 2.

TABLE 2

|  | Constituting materials of the hole-injecting layer | Driving voltage (V) | Half life (hr) |
|---|---|---|---|
| Example 7 | Formula (A-1) Formula (C-1) | 6.4 | 6,300 |
| Example 8 | Formula (A-9) | 6.5 | 6,500 |
| Example 9 | Formula (A-64) | 6.2 | 6,700 |
| Example 10 | Formula (A-94) | 6.3 | 6,000 |
| Comparative Example 1 | Formula (C-1) | 6.6 | 5,000 |

INDUSTRIAL APPLICABILITY

The material for an organic EL device of the invention is suitable as a constitution material of an organic EL device, in particular, as a material for a hole-transporting layer or a hole-injecting layer.

The organic EL device of the invention can be suitably used as a light source such as a planar emitting body and backlight of a display, a display part of a portable phone, PDA, a car navigator, or an instrument panel of an automobile, an illuminator, and the like.

The documents described in the specification are incorporated herein by reference in its entirety.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of the invention.

The invention claimed is:

1. A compound represented by formula (II):

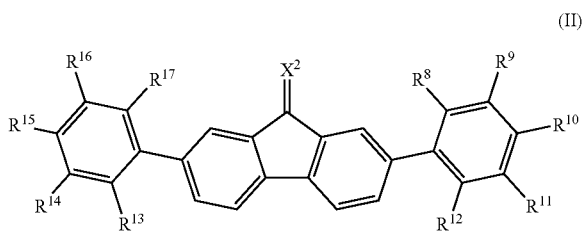

(II)

wherein $X^2$ is a divalent group represented by (a) or (b):

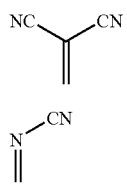

(a)

(b)

and $R^8$ to $R^{17}$ are independently a hydrogen atom, an alkyl group, an aryl group, a heterocycle, a halogen atom, a fluoroalkyl group or a cyano group

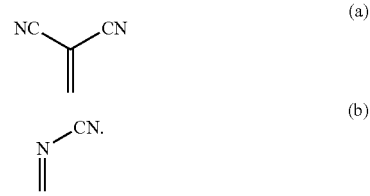

(a)

(b)

2. A material for an organic electroluminescence device, which is a hole-injecting material, comprising the compound of claim 1.

3. The compound according to claim 1, having a reductive potential in acetonitrile of −1.0V and more (vs Fc$^+$/Fc wherein Fc shows ferrocene).

4. An organic electroluminescence device comprising:
an anode and a cathode; and
one or plural organic thin film layers provided between the anode and the cathode, the organic thin film layers comprising an emitting layer;
wherein at least one layer of the organic thin film layers comprises the compound of formula (II) according to claim 1.

5. The organic electroluminescence device according to claim 4, wherein the organic thin film layers are a multilayer stack comprising a hole-transporting layer, an emitting layer and an electron-transporting layer in this order from the anode.

6. The organic electroluminescence device according to claim 5, wherein the hole-transporting layer comprises the compound of formula (II).

7. The organic electroluminescence device according to claim 4, wherein the organic thin film layers are a multilayer stack comprising a hole-injecting layer, a hole-transporting layer, an emitting layer and an electron-transporting layer in this order from the anode; and
the hole-injecting layer comprises the compound of formula (II).

8. The organic electroluminescence device according to claim 6, wherein the hole transporting layer further comprises a phenylenediamine compound represented by the following formula (IV);

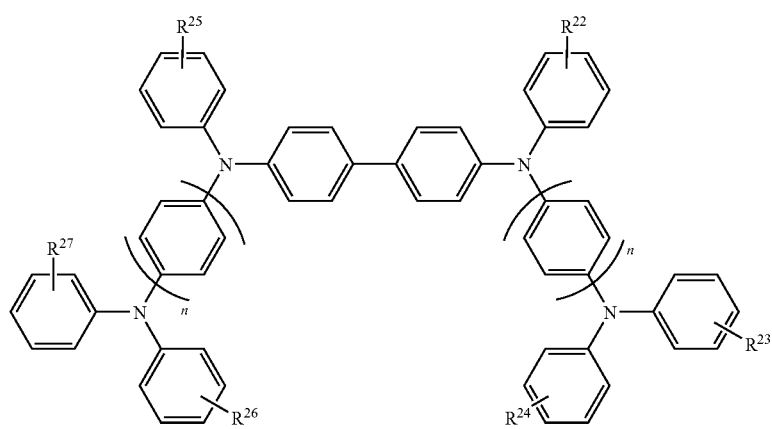

wherein $R^{22}$ to $R^{27}$ are independently a hydrogen atom, a halogen atom, a trifluoromethyl group, an alkyl group, an aryl group or a heterocycle, and $R^{22}$ to $R^{27}$ may form a naphthalene skeleton, a carbazole skeleton or a fluorene skeleton with a phenyl group bonded thereto; and n is 1 or 2.

9. The organic electroluminescence device according to claim 7, wherein the hole-injecting layer further comprises a phenylenediamine compound represented by the following formula (IV);

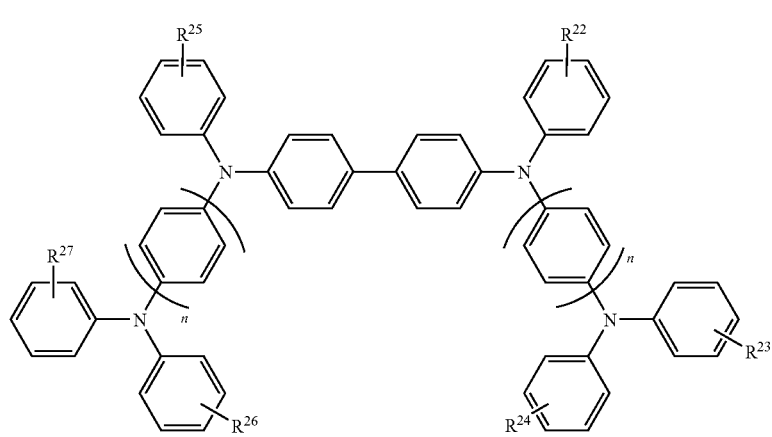

wherein $R^{22}$ to $R^{27}$ are independently a hydrogen atom, a halogen atom, a trifluoromethyl group, an alkyl group, an aryl group or a heterocycle, and $R^{22}$ to $R^{27}$ may form a naphthalene skeleton, a carbazole skeleton or a fluorene skeleton with a phenyl group bonded thereto; and n is 1 or 2.

10. An organic electroluminescence device comprising:
an anode and a cathode; and
one or plural organic thin film layers provided between the anode and the cathode, the organic thin film layers comprising an emitting layer;
wherein at least one layer of the organic thin film layers comprises the material according to claim 2.

11. The organic electroluminescence device according to claim 10, wherein the organic thin film layers are a multilayer stack comprising a hole-transporting layer, an emitting layer and an electron-transporting layer in this order from the anode.

12. The organic electroluminescence device according to claim 11, wherein the hole-transporting layer comprises the material for an organic electroluminescence device.

13. The organic electroluminescence device according to claim 10, wherein the organic thin film layers are a multilayer stack comprising a hole-injecting layer, a hole-transporting layer, an emitting layer and an electron-transporting layer in this order from the anode; and
the hole-injecting layer comprises the material for an organic electroluminescence device.

14. The organic electroluminescence device according to claim 12, wherein the hole transporting layer further comprises a phenylenediamine compound represented by the following formula (IV);

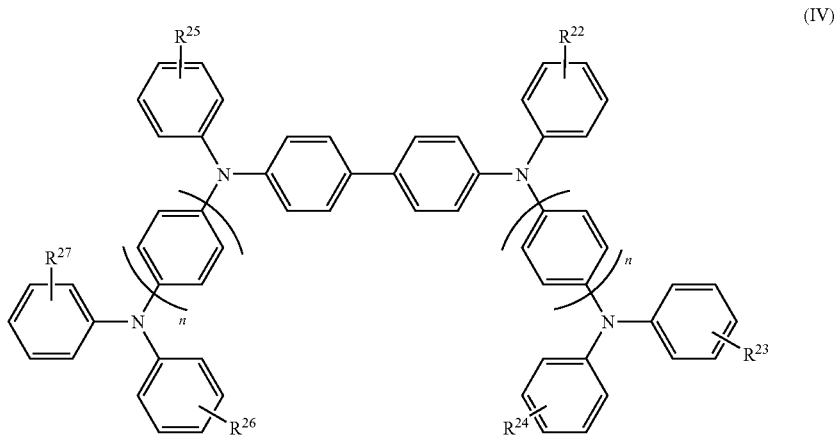

(IV)

wherein $R^{22}$ to $R^{27}$ are independently a hydrogen atom, a halogen atom, a trifluoromethyl group, an alkyl group, an aryl group or a heterocycle, and $R^{22}$ to $R^{27}$ may form a naphthalene skeleton, a carbazole skeleton or a fluorene skeleton with a phenyl group bonded thereto; and n is 1 or 2.

15. The organic electroluminescence device according to claim 13, wherein the hole-injecting layer further comprises a phenylenediamine compound represented by the following formula (IV);

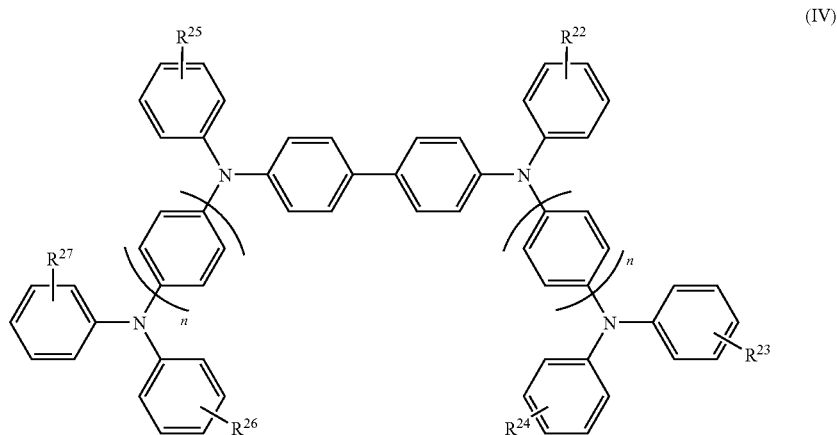

(IV)

wherein $R^{22}$ to $R^{27}$ are independently a hydrogen atom, a halogen atom, a trifluoromethyl group, an alkyl group, an aryl group or a heterocycle, and $R^{22}$ to $R^{27}$ may form a naphthalene skeleton, a carbazole skeleton or a fluorene skeleton with a phenyl group bonded thereto; and n is 1 or 2.

* * * * *